(12) United States Patent
Hoffman et al.

(10) Patent No.: US 8,585,715 B2
(45) Date of Patent: *Nov. 19, 2013

(54) ENDOSCOPIC APPARATUS WITH INTEGRATED VARICEAL LIGATION DEVICE

(75) Inventors: David W. Hoffman, Westborough, MA (US); Christopher Rowland, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/325,638

(22) Filed: Dec. 14, 2011

(65) Prior Publication Data

US 2012/0150196 A1 Jun. 14, 2012

Related U.S. Application Data

(63) Continuation of application No. 11/129,225, filed on May 13, 2005, now Pat. No. 8,097,003.

(51) Int. Cl.
*A61B 17/10* (2006.01)

(52) U.S. Cl.
USPC .......................................... 606/140

(58) Field of Classification Search
USPC ................. 606/140, 139, 144, 148, 228, 138; 29/235, 229, 812
See application file for complete search history.

(56) References Cited

U.S. PATENT DOCUMENTS

| | | | |
|---|---|---|---|
| 3,266,059 A | 8/1966 | Stelle | |
| 3,470,876 A | 10/1969 | Barchilon | |
| 3,572,325 A | 3/1971 | Bazell et al. | |
| 3,581,738 A | 6/1971 | Moore | |
| 4,108,211 A | 8/1978 | Tanaka | |
| 4,286,585 A | 9/1981 | Ogawa | |
| 4,294,162 A | 10/1981 | Fowler et al. | |
| 4,315,309 A | 2/1982 | Coli | |
| 4,351,323 A | 9/1982 | Ouchi et al. | |
| 4,425,113 A | 1/1984 | Bilstad | |
| 4,432,349 A | 2/1984 | Oshiro | |
| 4,471,766 A | 9/1984 | Terayama | |
| 4,473,841 A | 9/1984 | Murakoshi et al. | |
| 4,488,039 A | 12/1984 | Sato et al. | |
| 4,491,865 A | 1/1985 | Danna et al. | |
| 4,495,134 A | 1/1985 | Ouchi et al. | |
| 4,499,895 A | 2/1985 | Takayama | |
| 4,513,235 A | 4/1985 | Acklam et al. | |

(Continued)

FOREIGN PATENT DOCUMENTS

| | | |
|---|---|---|
| EP | 0 689 851 | 1/1996 |
| EP | 1 147 744 | 10/2001 |

(Continued)

*Primary Examiner* — S. Thomas Hughes
*Assistant Examiner* — Tin Nguyen
(74) *Attorney, Agent, or Firm* — Bookoff McAndrews, PLLC

(57) ABSTRACT

A variceal banding endoscope includes an elongated shaft having a distal end and a proximal end that is removably connected to a control unit. The endoscope includes a variceal banding apparatus fixedly attached to the distal end of the endoscope and capable of receiving a plurality of ligation bands. A trigger cable extends from the proximal end to the distal end of the shaft and is digitally actuated by an actuator in the control unit or handle of the scope in response to a user input device.

19 Claims, 11 Drawing Sheets

(56) References Cited

U.S. PATENT DOCUMENTS

| | | | |
|---|---|---|---|
| 4,515,444 | A | 5/1985 | Prescott et al. |
| 4,516,063 | A | 5/1985 | Kaye et al. |
| 4,519,391 | A | 5/1985 | Murakoshi |
| 4,559,928 | A | 12/1985 | Takayama |
| 4,573,450 | A | 3/1986 | Arakawa |
| 4,580,210 | A | 4/1986 | Nordstrom |
| 4,586,923 | A | 5/1986 | Gould et al. |
| 4,615,330 | A | 10/1986 | Nagasaki et al. |
| 4,616,630 | A | 10/1986 | Arakawa |
| 4,617,915 | A | 10/1986 | Arakawa |
| 4,621,618 | A | 11/1986 | Omagari et al. |
| 4,625,714 | A | 12/1986 | Toyota |
| 4,631,582 | A | 12/1986 | Nagasaki et al. |
| 4,633,303 | A | 12/1986 | Nagasaki et al. |
| 4,633,304 | A | 12/1986 | Nagasaki |
| 4,643,170 | A | 2/1987 | Miyazaki et al. |
| 4,646,723 | A | 3/1987 | Arakawa |
| 4,649,904 | A | 3/1987 | Krauter et al. |
| 4,651,202 | A | 3/1987 | Arakawa |
| 4,652,093 | A | 3/1987 | Stephen et al. |
| 4,652,916 | A | 3/1987 | Suzaki et al. |
| 4,654,701 | A | 3/1987 | Yabe |
| RE32,421 | E | 5/1987 | Hattori |
| 4,662,725 | A | 5/1987 | Nisioka |
| 4,663,657 | A | 5/1987 | Nagasaki et al. |
| 4,667,655 | A | 5/1987 | Ogiu et al. |
| 4,674,844 | A | 6/1987 | Nishioka et al. |
| 4,686,963 | A | 8/1987 | Cohen et al. |
| 4,697,210 | A | 9/1987 | Toyota et al. |
| 4,700,693 | A | 10/1987 | Lia et al. |
| 4,714,075 | A | 12/1987 | Krauter et al. |
| 4,716,457 | A | 12/1987 | Matsuo |
| 4,719,508 | A | 1/1988 | Sasaki et al. |
| 4,727,417 | A | 2/1988 | Kanno et al. |
| 4,727,418 | A | 2/1988 | Kato et al. |
| 4,745,470 | A | 5/1988 | Yabe et al. |
| 4,745,471 | A | 5/1988 | Takamura et al. |
| 4,746,974 | A | 5/1988 | Matsuo |
| 4,748,970 | A | 6/1988 | Nakajima |
| 4,755,029 | A | 7/1988 | Okabe |
| 4,762,119 | A | 8/1988 | Allred et al. |
| 4,765,312 | A | 8/1988 | Sasa et al. |
| 4,766,489 | A | 8/1988 | Kato |
| 4,787,369 | A | 11/1988 | Allred et al. |
| 4,790,294 | A | 12/1988 | Allred et al. |
| 4,794,913 | A | 1/1989 | Shimonaka et al. |
| 4,796,607 | A | 1/1989 | Allred et al. |
| 4,800,869 | A | 1/1989 | Nakajima |
| 4,805,596 | A | 2/1989 | Hatori |
| 4,806,011 | A | 2/1989 | Bettinger |
| 4,819,065 | A | 4/1989 | Eino |
| 4,819,077 | A | 4/1989 | Kikuchi et al. |
| 4,821,116 | A | 4/1989 | Nagasaki et al. |
| 4,824,225 | A | 4/1989 | Nishioka |
| 4,831,437 | A | 5/1989 | Nishioka et al. |
| 4,836,187 | A | 6/1989 | Iwakoshi et al. |
| 4,844,052 | A | 7/1989 | Iwakoshi et al. |
| 4,845,553 | A | 7/1989 | Konomura et al. |
| 4,845,555 | A | 7/1989 | Yabe et al. |
| 4,847,694 | A | 7/1989 | Nishihara |
| 4,853,772 | A | 8/1989 | Kikuchi |
| 4,860,731 | A | 8/1989 | Matsuura |
| 4,867,546 | A | 9/1989 | Nishioka et al. |
| 4,868,647 | A | 9/1989 | Uehara et al. |
| 4,869,237 | A | 9/1989 | Eino et al. |
| 4,873,965 | A | 10/1989 | Danieli |
| 4,875,468 | A | 10/1989 | Krauter et al. |
| 4,877,314 | A | 10/1989 | Kanamori |
| 4,882,623 | A | 11/1989 | Uchikubo |
| 4,884,134 | A | 11/1989 | Tsuji et al. |
| 4,885,634 | A | 12/1989 | Yabe |
| 4,890,159 | A | 12/1989 | Ogiu |
| 4,894,715 | A | 1/1990 | Uchikubo et al. |
| 4,895,431 | A | 1/1990 | Tsujiuchi et al. |
| 4,899,731 | A | 2/1990 | Takayama et al. |
| 4,899,732 | A | 2/1990 | Cohen |
| 4,899,787 | A | 2/1990 | Ouchi et al. |
| 4,905,666 | A | 3/1990 | Fukuda |
| 4,918,521 | A | 4/1990 | Yabe et al. |
| 4,919,112 | A | 4/1990 | Siegmund |
| 4,919,114 | A | 4/1990 | Miyazaki |
| 4,920,980 | A | 5/1990 | Jackowski |
| 4,928,172 | A | 5/1990 | Uehara et al. |
| 4,931,867 | A | 6/1990 | Kikuchi |
| 4,941,454 | A | 7/1990 | Wood et al. |
| 4,941,456 | A | 7/1990 | Wood et al. |
| 4,951,134 | A | 8/1990 | Nakasima et al. |
| 4,951,135 | A | 8/1990 | Sasagawa et al. |
| 4,952,040 | A | 8/1990 | Igarashi |
| 4,960,127 | A | 10/1990 | Noce et al. |
| 4,961,110 | A | 10/1990 | Nakamura |
| 4,967,269 | A | 10/1990 | Sasagawa et al. |
| 4,971,034 | A | 11/1990 | Doi et al. |
| 4,973,311 | A | 11/1990 | Iwakoshi et al. |
| 4,979,497 | A | 12/1990 | Matsuura et al. |
| 4,982,725 | A | 1/1991 | Hibino et al. |
| 4,984,878 | A | 1/1991 | Miyano |
| 4,986,642 | A | 1/1991 | Yokota et al. |
| 4,987,884 | A | 1/1991 | Nishioka et al. |
| 4,989,075 | A | 1/1991 | Ito |
| 4,989,581 | A | 2/1991 | Tamburrino et al. |
| 4,996,974 | A | 3/1991 | Ciarlei |
| 4,996,975 | A | 3/1991 | Nakamura |
| 5,001,556 | A | 3/1991 | Nakamura et al. |
| 5,005,558 | A | 4/1991 | Aomori |
| 5,005,957 | A | 4/1991 | Kanamori et al. |
| 5,007,408 | A | 4/1991 | Ieoka |
| 5,018,509 | A | 5/1991 | Suzuki et al. |
| 5,022,382 | A | 6/1991 | Ohshoki et al. |
| 5,029,016 | A | 7/1991 | Hiyama et al. |
| 5,034,888 | A | 7/1991 | Uehara et al. |
| 5,040,069 | A | 8/1991 | Matsumoto et al. |
| RE33,689 | E | 9/1991 | Nishioka et al. |
| 5,045,935 | A | 9/1991 | Kikuchi |
| 5,049,989 | A | 9/1991 | Tsuji |
| 5,050,584 | A | 9/1991 | Matsuura |
| 5,050,974 | A | 9/1991 | Takasugi et al. |
| 5,056,503 | A | 10/1991 | Nagasaki |
| 5,061,994 | A | 10/1991 | Takahashi |
| 5,068,719 | A | 11/1991 | Tsuji |
| 5,081,524 | A | 1/1992 | Tsuruoka et al. |
| 5,087,989 | A | 2/1992 | Igarashi |
| 5,110,645 | A | 5/1992 | Matsumoto et al. |
| 5,111,281 | A | 5/1992 | Sekiguchi |
| 5,111,306 | A | 5/1992 | Kanno et al. |
| 5,111,804 | A | 5/1992 | Funakoshi |
| 5,113,254 | A | 5/1992 | Kanno et al. |
| 5,119,238 | A | 6/1992 | Igarashi |
| 5,131,393 | A | 7/1992 | Ishiguro et al. |
| 5,137,013 | A | 8/1992 | Chiba et al. |
| 5,140,265 | A | 8/1992 | Sakiyama et al. |
| 5,159,446 | A | 10/1992 | Hibino et al. |
| 5,170,775 | A | 12/1992 | Tagami |
| 5,172,225 | A | 12/1992 | Takahashi et al. |
| 5,174,293 | A | 12/1992 | Hagiwara |
| 5,176,629 | A | 1/1993 | Kullas et al. |
| 5,191,878 | A | 3/1993 | Iida et al. |
| 5,198,931 | A | 3/1993 | Igarashi |
| 5,201,908 | A | 4/1993 | Jones |
| 5,208,702 | A | 5/1993 | Shiraiwa |
| 5,209,220 | A | 5/1993 | Hiyama et al. |
| 5,225,958 | A | 7/1993 | Nakamura |
| 5,228,356 | A | 7/1993 | Chuang |
| 5,243,416 | A | 9/1993 | Nakazawa |
| 5,243,967 | A | 9/1993 | Hibino |
| 5,257,628 | A | 11/1993 | Ishiguro et al. |
| 5,271,381 | A | 12/1993 | Ailinger et al. |
| RE34,504 | E | 1/1994 | Uehara et al. |
| 5,291,010 | A | 3/1994 | Tsuji |
| 5,299,559 | A | 4/1994 | Bruce et al. |
| 5,311,858 | A | 5/1994 | Adair |
| 5,325,845 | A | 7/1994 | Adair et al. |
| 5,331,551 | A | 7/1994 | Tsuruoka et al. |
| 5,342,299 | A | 8/1994 | Snoke et al. |

(56) References Cited

U.S. PATENT DOCUMENTS

| | | |
|---|---|---|
| 5,347,989 A | 9/1994 | Monroe et al. |
| 5,374,953 A | 12/1994 | Sasaki et al. |
| 5,379,757 A | 1/1995 | Hiyama et al. |
| 5,381,782 A | 1/1995 | DeLaRama et al. |
| 5,390,662 A | 2/1995 | Okada |
| 5,400,769 A | 3/1995 | Tanii et al. |
| 5,402,768 A | 4/1995 | Adair |
| 5,402,769 A | 4/1995 | Tsuji |
| 5,409,485 A | 4/1995 | Suda |
| 5,412,478 A | 5/1995 | Ishihara et al. |
| 5,418,649 A | 5/1995 | Igarashi |
| 5,420,644 A | 5/1995 | Watanabe |
| 5,431,645 A | 7/1995 | Smith et al. |
| 5,434,615 A | 7/1995 | Matumoto |
| 5,436,640 A | 7/1995 | Reeves |
| 5,436,767 A | 7/1995 | Suzuki et al. |
| 5,440,341 A | 8/1995 | Suzuki et al. |
| 5,464,007 A | 11/1995 | Krauter et al. |
| 5,469,840 A | 11/1995 | Tanii et al. |
| 5,473,235 A | 12/1995 | Lance et al. |
| 5,482,029 A | 1/1996 | Sekiguchi et al. |
| 5,484,407 A | 1/1996 | Osypka |
| 5,485,316 A | 1/1996 | Mori et al. |
| 5,496,260 A | 3/1996 | Krauter et al. |
| 5,515,449 A | 5/1996 | Tsuruoka et al. |
| 5,518,501 A | 5/1996 | Oneda et al. |
| 5,543,831 A | 8/1996 | Tsuji et al. |
| 5,569,158 A | 10/1996 | Suzuki et al. |
| 5,569,159 A | 10/1996 | Anderson et al. |
| 5,586,262 A | 12/1996 | Komatsu et al. |
| 5,589,854 A | 12/1996 | Tsai |
| 5,591,202 A | 1/1997 | Slater et al. |
| 5,608,451 A | 3/1997 | Konno et al. |
| 5,619,380 A | 4/1997 | Ogasawara et al. |
| 5,622,528 A | 4/1997 | Hamano et al. |
| 5,624,453 A * | 4/1997 | Ahmed .................. 606/140 |
| 5,631,695 A | 5/1997 | Nakamura et al. |
| 5,633,203 A | 5/1997 | Adair |
| 5,643,203 A | 7/1997 | Beiser et al. |
| 5,645,075 A | 7/1997 | Palmer et al. |
| 5,647,840 A | 7/1997 | D'Amelio et al. |
| 5,658,238 A | 8/1997 | Suzuki et al. |
| 5,667,477 A | 9/1997 | Segawa |
| 5,674,182 A | 10/1997 | Suzuki et al. |
| 5,674,197 A | 10/1997 | van Muiden et al. |
| 5,676,673 A | 10/1997 | Ferre et al. |
| 5,685,823 A | 11/1997 | Ito et al. |
| 5,685,825 A | 11/1997 | Takase et al. |
| 5,691,853 A | 11/1997 | Miyano |
| 5,695,450 A | 12/1997 | Yabe et al. |
| 5,698,866 A | 12/1997 | Doiron et al. |
| 5,702,349 A | 12/1997 | Morizumi |
| 5,703,724 A | 12/1997 | Miyano |
| 5,704,371 A | 1/1998 | Shepard |
| 5,704,896 A | 1/1998 | Fukunishi et al. |
| 5,708,482 A | 1/1998 | Takahashi et al. |
| 5,721,566 A | 2/1998 | Rosenberg et al. |
| 5,724,068 A | 3/1998 | Sanchez et al. |
| 5,728,045 A | 3/1998 | Komi |
| 5,739,811 A | 4/1998 | Rosenberg et al. |
| 5,740,801 A | 4/1998 | Branson |
| 5,746,696 A | 5/1998 | Kondo |
| 5,764,809 A | 6/1998 | Nomami et al. |
| 5,767,839 A | 6/1998 | Rosenberg |
| 5,781,172 A | 7/1998 | Engel et al. |
| 5,788,714 A | 8/1998 | Ouchi |
| 5,789,047 A | 8/1998 | Sasaki et al. |
| 5,793,539 A | 8/1998 | Konno et al. |
| 5,805,140 A | 9/1998 | Rosenberg et al. |
| 5,810,715 A | 9/1998 | Moriyama |
| 5,812,983 A | 9/1998 | Kumagai |
| 5,819,736 A | 10/1998 | Avny et al. |
| 5,820,591 A | 10/1998 | Thompson et al. |
| 5,821,466 A | 10/1998 | Clark et al. |
| 5,821,920 A | 10/1998 | Rosenberg et al. |
| 5,823,948 A | 10/1998 | Ross, Jr. et al. |
| 5,827,186 A | 10/1998 | Chen et al. |
| 5,827,190 A | 10/1998 | Palcic et al. |
| 5,828,197 A | 10/1998 | Martin et al. |
| 5,828,363 A | 10/1998 | Yaniger et al. |
| 5,830,124 A | 11/1998 | Suzuki et al. |
| 5,830,128 A | 11/1998 | Tanaka |
| 5,836,869 A | 11/1998 | Kudo et al. |
| 5,837,023 A | 11/1998 | Koike et al. |
| 5,840,014 A | 11/1998 | Miyano et al. |
| 5,841,126 A | 11/1998 | Fossum et al. |
| 5,843,000 A | 12/1998 | Nishioka et al. |
| 5,846,183 A | 12/1998 | Chilcoat |
| 5,855,560 A | 1/1999 | Idaomi et al. |
| 5,857,585 A * | 1/1999 | Tolkoff et al. .................. 221/36 |
| 5,857,963 A | 1/1999 | Pelchy et al. |
| 5,865,724 A | 2/1999 | Palmer et al. |
| 5,868,664 A | 2/1999 | Speier et al. |
| 5,868,666 A | 2/1999 | Okada et al. |
| 5,873,816 A | 2/1999 | Kagawa et al. |
| 5,873,866 A | 2/1999 | Kondo et al. |
| 5,876,326 A | 3/1999 | Takamura et al. |
| 5,876,331 A | 3/1999 | Wu et al. |
| 5,876,373 A | 3/1999 | Giba et al. |
| 5,876,427 A | 3/1999 | Chen et al. |
| 5,877,819 A | 3/1999 | Branson |
| 5,879,284 A | 3/1999 | Tsujita |
| 5,880,714 A | 3/1999 | Rosenberg et al. |
| 5,882,293 A | 3/1999 | Ouchi |
| 5,882,339 A | 3/1999 | Beiser et al. |
| 5,889,670 A | 3/1999 | Schuler et al. |
| 5,889,672 A | 3/1999 | Schuler et al. |
| 5,892,630 A | 4/1999 | Broome |
| 5,895,350 A | 4/1999 | Hori |
| 5,897,507 A | 4/1999 | Kortenbach et al. |
| 5,897,525 A | 4/1999 | Dey et al. |
| 5,907,487 A | 5/1999 | Rosenberg et al. |
| 5,923,018 A | 7/1999 | Kameda et al. |
| 5,928,136 A | 7/1999 | Barry |
| 5,929,607 A | 7/1999 | Rosenberg et al. |
| 5,929,846 A | 7/1999 | Rosenberg et al. |
| 5,929,900 A | 7/1999 | Yamanaka |
| 5,929,901 A | 7/1999 | Adair et al. |
| 5,931,833 A | 8/1999 | Silverstein |
| 5,933,809 A | 8/1999 | Hunt et al. |
| 5,935,085 A | 8/1999 | Welsh et al. |
| 5,936,778 A | 8/1999 | Miyano et al. |
| 5,941,817 A | 8/1999 | Crawford |
| 5,950,168 A | 9/1999 | Simborg et al. |
| 5,951,462 A | 9/1999 | Yamanaka |
| 5,956,416 A | 9/1999 | Tsuruoka et al. |
| 5,956,689 A | 9/1999 | Everhart |
| 5,956,690 A | 9/1999 | Haggerson et al. |
| 5,959,613 A | 9/1999 | Rosenberg et al. |
| 5,968,056 A * | 10/1999 | Chu et al. .................. 606/140 |
| 5,976,070 A | 11/1999 | Ono et al. |
| 5,976,074 A | 11/1999 | Moriyama |
| 5,980,454 A | 11/1999 | Broome |
| 5,980,468 A | 11/1999 | Zimmon |
| 5,986,693 A | 11/1999 | Adair et al. |
| 5,991,729 A | 11/1999 | Barry et al. |
| 5,991,730 A | 11/1999 | Lubin et al. |
| 5,999,168 A | 12/1999 | Rosenberg et al. |
| 6,002,425 A | 12/1999 | Yamanaka et al. |
| 6,007,531 A | 12/1999 | Snoke et al. |
| 6,014,630 A | 1/2000 | Jeacock et al. |
| 6,015,088 A | 1/2000 | Parker et al. |
| 6,017,322 A | 1/2000 | Snoke et al. |
| 6,020,875 A | 2/2000 | Moore et al. |
| 6,020,876 A | 2/2000 | Rosenberg et al. |
| 6,026,363 A | 2/2000 | Shepard |
| 6,030,360 A | 2/2000 | Biggs |
| 6,032,120 A | 2/2000 | Rock et al. |
| 6,039,728 A | 3/2000 | Berlien et al. |
| 6,043,839 A | 3/2000 | Adair et al. |
| 6,050,718 A | 4/2000 | Schena et al. |
| 6,057,828 A | 5/2000 | Schena et al. |
| 6,059,719 A | 5/2000 | Yamamoto et al. |
| 6,061,004 A | 5/2000 | Rosenberg |

(56) References Cited

U.S. PATENT DOCUMENTS

| | | |
|---|---|---|
| 6,066,145 A * | 5/2000 | Wurster .................. 606/141 |
| 6,067,077 A | 5/2000 | Martin et al. |
| 6,071,248 A | 6/2000 | Zimmon |
| 6,075,555 A | 6/2000 | Street |
| 6,078,308 A | 6/2000 | Rosenberg et al. |
| 6,078,353 A | 6/2000 | Yamanaka et al. |
| 6,078,876 A | 6/2000 | Rosenberg et al. |
| 6,080,104 A | 6/2000 | Ozawa et al. |
| 6,081,809 A | 6/2000 | Kumagai |
| 6,083,152 A | 7/2000 | Strong |
| 6,083,170 A | 7/2000 | Ben-Haim |
| 6,095,971 A | 8/2000 | Takahashi |
| 6,099,465 A | 8/2000 | Inoue |
| 6,100,874 A | 8/2000 | Schena et al. |
| 6,104,382 A | 8/2000 | Martin et al. |
| 6,120,435 A | 9/2000 | Eino |
| 6,125,337 A | 9/2000 | Rosenberg et al. |
| 6,128,006 A | 10/2000 | Rosenberg et al. |
| 6,132,369 A | 10/2000 | Takahashi |
| 6,134,056 A | 10/2000 | Nakamuka |
| 6,134,506 A | 10/2000 | Rosenberg et al. |
| 6,135,946 A | 10/2000 | Konen et al. |
| 6,139,508 A | 10/2000 | Simpson et al. |
| 6,141,037 A | 10/2000 | Upton et al. |
| 6,142,956 A | 11/2000 | Kortenbach et al. |
| 6,146,355 A | 11/2000 | Biggs |
| 6,149,607 A | 11/2000 | Simpson et al. |
| 6,152,877 A | 11/2000 | Masters |
| 6,154,198 A | 11/2000 | Rosenberg |
| 6,154,248 A | 11/2000 | Ozawa et al. |
| 6,155,988 A | 12/2000 | Peters |
| 6,181,481 B1 | 1/2001 | Yamamoto et al. |
| 6,184,922 B1 | 2/2001 | Saito et al. |
| 6,193,714 B1 | 2/2001 | McGaffigan et al. |
| 6,195,592 B1 | 2/2001 | Schuler et al. |
| 6,203,493 B1 | 3/2001 | Ben-Haim |
| 6,206,824 B1 | 3/2001 | Ohara et al. |
| 6,211,904 B1 | 4/2001 | Adair |
| 6,216,104 B1 | 4/2001 | Moshfeghi et al. |
| 6,219,091 B1 | 4/2001 | Yamanaka et al. |
| 6,221,070 B1 | 4/2001 | Tu et al. |
| 6,241,668 B1 | 6/2001 | Herzog |
| 6,260,994 B1 | 7/2001 | Matsumoto et al. |
| 6,272,470 B1 | 8/2001 | Teshima |
| 6,275,255 B1 | 8/2001 | Adair et al. |
| 6,283,960 B1 | 9/2001 | Ashley |
| 6,295,082 B1 | 9/2001 | Dowdy et al. |
| 6,299,625 B1 | 10/2001 | Bacher |
| 6,309,347 B1 | 10/2001 | Takahashi et al. |
| 6,310,642 B1 | 10/2001 | Adair et al. |
| 6,319,196 B1 | 11/2001 | Minami |
| 6,319,197 B1 | 11/2001 | Tsuji et al. |
| 6,334,844 B1 | 1/2002 | Akiba |
| 6,346,075 B1 | 2/2002 | Arai et al. |
| 6,366,799 B1 | 4/2002 | Acker et al. |
| 6,381,029 B1 | 4/2002 | Tipirneni |
| 6,398,724 B1 | 6/2002 | May et al. |
| 6,413,207 B1 | 7/2002 | Minami |
| 6,421,078 B1 | 7/2002 | Akai et al. |
| 6,425,535 B1 | 7/2002 | Akiba |
| 6,425,858 B1 | 7/2002 | Minami |
| 6,436,032 B1 | 8/2002 | Eto et al. |
| 6,441,845 B1 | 8/2002 | Matsumoto |
| 6,447,444 B1 | 9/2002 | Avni et al. |
| 6,449,006 B1 | 9/2002 | Shipp |
| 6,453,190 B1 | 9/2002 | Acker et al. |
| 6,454,162 B1 | 9/2002 | Teller |
| 6,459,447 B1 | 10/2002 | Okada et al. |
| 6,468,204 B2 | 10/2002 | Sendai et al. |
| 6,475,141 B2 | 11/2002 | Abe |
| 6,478,730 B1 | 11/2002 | Bala et al. |
| 6,489,987 B1 | 12/2002 | Higuchi et al. |
| 6,496,827 B2 | 12/2002 | Kozam et al. |
| 6,498,948 B1 | 12/2002 | Ozawa et al. |
| 6,503,193 B1 | 1/2003 | Iwasaki et al. |
| 6,520,908 B1 | 2/2003 | Ikeda et al. |
| 6,524,234 B2 | 2/2003 | Ouchi |
| 6,526,979 B1 | 3/2003 | Nikolchev et al. |
| 6,530,882 B1 | 3/2003 | Farkas et al. |
| 6,533,722 B2 | 3/2003 | Nakashima |
| 6,540,669 B2 | 4/2003 | Abe et al. |
| 6,544,194 B2 | 4/2003 | Kortenbach et al. |
| 6,545,703 B1 | 4/2003 | Takahashi et al. |
| 6,551,239 B2 | 4/2003 | Renner et al. |
| 6,558,317 B2 | 5/2003 | Takahashi et al. |
| 6,561,971 B1 | 5/2003 | Akiba |
| 6,565,507 B2 | 5/2003 | Kamata et al. |
| 6,574,629 B1 | 6/2003 | Cooke, Jr. et al. |
| 6,589,162 B2 | 7/2003 | Nakashima et al. |
| 6,594,971 B1 | 7/2003 | Addy et al. |
| 6,595,913 B2 | 7/2003 | Takahashi |
| 6,597,390 B1 | 7/2003 | Higuchi |
| 6,599,239 B2 | 7/2003 | Hayakawa et al. |
| 6,602,186 B1 | 8/2003 | Sugimoto et al. |
| 6,605,035 B2 | 8/2003 | Ando et al. |
| 6,609,135 B1 | 8/2003 | Omori et al. |
| 6,611,846 B1 | 8/2003 | Stoodley |
| 6,614,969 B2 | 9/2003 | Eichelberger et al. |
| 6,616,601 B2 | 9/2003 | Hayakawa |
| 6,623,424 B2 | 9/2003 | Hayakawa et al. |
| 6,638,214 B2 | 10/2003 | Akiba |
| 6,638,215 B2 | 10/2003 | Kobayashi |
| 6,641,528 B2 | 11/2003 | Torii |
| 6,651,669 B1 | 11/2003 | Burnside |
| 6,656,110 B1 | 12/2003 | Irion et al. |
| 6,656,112 B2 | 12/2003 | Miyanaga |
| 6,659,940 B2 | 12/2003 | Adler |
| 6,663,561 B2 | 12/2003 | Sugimoto et al. |
| 6,669,629 B2 | 12/2003 | Matsui |
| 6,673,012 B2 | 1/2004 | Fujii et al. |
| 6,676,672 B2 | 1/2004 | Chu et al. |
| 6,677,984 B2 | 1/2004 | Kobayashi et al. |
| 6,678,397 B1 | 1/2004 | Ohmori et al. |
| 6,682,479 B1 | 1/2004 | Takahashi et al. |
| 6,685,631 B2 | 2/2004 | Minami |
| 6,685,713 B1 * | 2/2004 | Ahmed .................. 606/140 |
| 6,686,949 B2 | 2/2004 | Kobayashi et al. |
| 6,690,409 B1 | 2/2004 | Takahashi |
| 6,690,963 B2 | 2/2004 | Ben-Haim et al. |
| 6,692,431 B2 | 2/2004 | Kazakevich |
| 6,697,101 B1 | 2/2004 | Takahashi et al. |
| 6,699,181 B2 | 3/2004 | Wako |
| 6,702,737 B2 | 3/2004 | Hinto et al. |
| 6,711,426 B2 | 3/2004 | Benaron et al. |
| 6,715,068 B1 | 3/2004 | Abe |
| 6,716,162 B2 | 4/2004 | Hakamata |
| 6,728,599 B2 | 4/2004 | Wang et al. |
| 6,730,018 B2 | 5/2004 | Takase |
| 6,736,773 B2 | 5/2004 | Wendlandt et al. |
| 6,743,240 B2 | 6/2004 | Smith et al. |
| 6,749,559 B1 | 6/2004 | Kraas et al. |
| 6,749,560 B1 | 6/2004 | Konstorum et al. |
| 6,749,561 B2 | 6/2004 | Kazakevich |
| 6,753,905 B1 | 6/2004 | Okada et al. |
| 6,758,806 B2 | 7/2004 | Kamrava et al. |
| 6,758,807 B2 | 7/2004 | Minami |
| 6,758,842 B2 | 7/2004 | Irion et al. |
| 6,778,208 B2 | 8/2004 | Takeshige et al. |
| 6,780,151 B2 | 8/2004 | Grabover et al. |
| 6,785,410 B2 | 8/2004 | Vining et al. |
| 6,785,593 B2 | 8/2004 | Wang et al. |
| 6,796,938 B2 | 9/2004 | Sendai |
| 6,796,939 B1 | 9/2004 | Hirata et al. |
| 6,798,533 B2 | 9/2004 | Tipirneni |
| 6,800,056 B2 | 10/2004 | Tartaglia et al. |
| 6,800,057 B2 | 10/2004 | Tsujita et al. |
| 6,808,491 B2 | 10/2004 | Kortenbach et al. |
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang et al. |
| 6,842,196 B1 | 1/2005 | Swift et al. |

(56) References Cited

U.S. PATENT DOCUMENTS

| | | |
|---|---|---|
| 6,846,286 B2 | 1/2005 | Suzuki et al. |
| 6,847,933 B1 | 1/2005 | Hastings |
| 6,849,043 B2 | 2/2005 | Kondo |
| 6,850,794 B2 | 2/2005 | Shahidi |
| 6,855,109 B2 | 2/2005 | Obata et al. |
| 6,858,004 B1 | 2/2005 | Ozawa et al. |
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayashi et al. |
| 6,932,761 B2 | 8/2005 | Maeda et al. |
| 6,934,093 B2 | 8/2005 | Kisley et al. |
| 6,934,575 B2 | 8/2005 | Ferre et al. |
| 6,943,663 B2 | 9/2005 | Wang et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,691 B2 | 9/2005 | Uchikubo |
| 6,955,671 B2 | 10/2005 | Uchikubo |
| 7,189,247 B1 | 3/2007 | Zirps et al. |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0072757 A1 | 6/2002 | Ahmed et al. |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0193664 A1 | 12/2002 | Ross et al. |
| 2003/0034863 A1 | 2/2003 | Ono et al. |
| 2003/0069897 A1 | 4/2003 | Roy et al. |
| 2003/0149338 A1 | 8/2003 | Francois et al. |
| 2003/0181905 A1 | 9/2003 | Long |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Maeda et al. |
| 2004/0073085 A1 | 4/2004 | Ikeda et al. |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tipirneni |
| 2005/0075538 A1 | 4/2005 | Banik |
| 2005/0119527 A1 | 6/2005 | Banik et al. |
| 2005/0197861 A1 | 9/2005 | Omori et al. |
| 2005/0203341 A1 | 9/2005 | Welker et al. |
| 2005/0228697 A1 | 10/2005 | Funahashi |

FOREIGN PATENT DOCUMENTS

| | | |
|---|---|---|
| EP | 1 300 883 | 4/2003 |
| JP | 58-78635 | 5/1983 |
| JP | 05-31071 | 2/1993 |
| JP | 05-091972 | 4/1993 |
| JP | 06-105800 | 4/1994 |
| JP | 06-254048 | 9/1994 |
| JP | 07-8441 | 1/1995 |
| JP | 10-113330 | 5/1998 |
| JP | 10-286221 | 10/1998 |
| JP | 11-216113 | 8/1999 |
| JP | 3219521 | 8/2001 |
| JP | 2002-102152 | 4/2002 |
| JP | 2002-177197 | 6/2002 |
| JP | 2002-185873 | 6/2002 |
| JP | 2002-253481 | 9/2002 |
| JP | 3372273 | 11/2002 |
| JP | 2003-75113 | 3/2003 |
| JP | 3482238 | 10/2003 |
| WO | WO 93/13704 | 7/1993 |
| WO | WO 00/10456 | 3/2000 |
| WO | WO 2004/016310 | 2/2004 |
| WO | WO 2005/023082 | 3/2005 |

\* cited by examiner

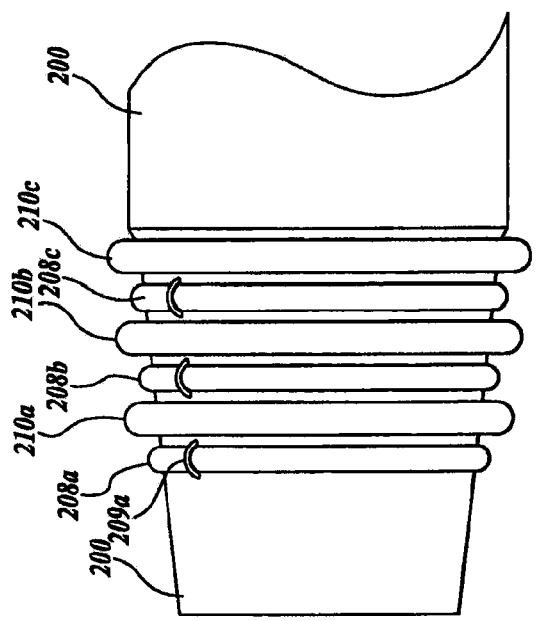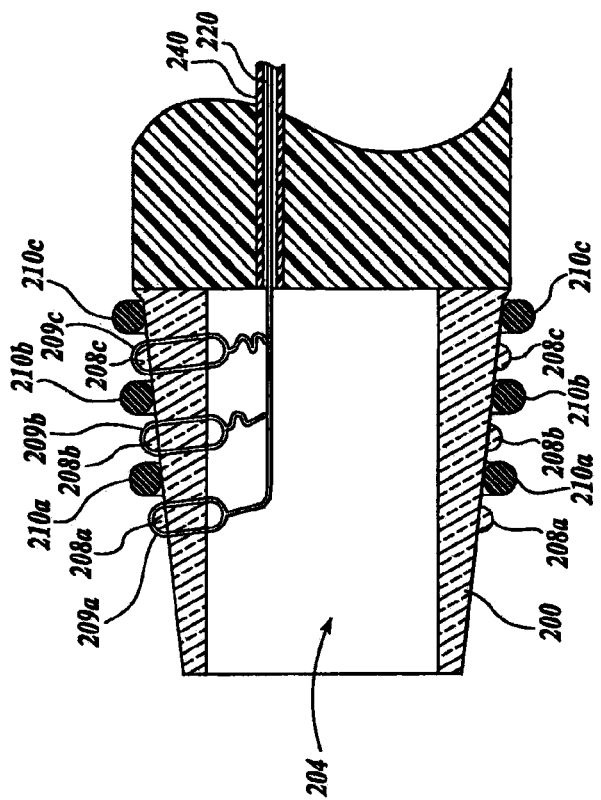
Fig.3C.
Fig.3D.

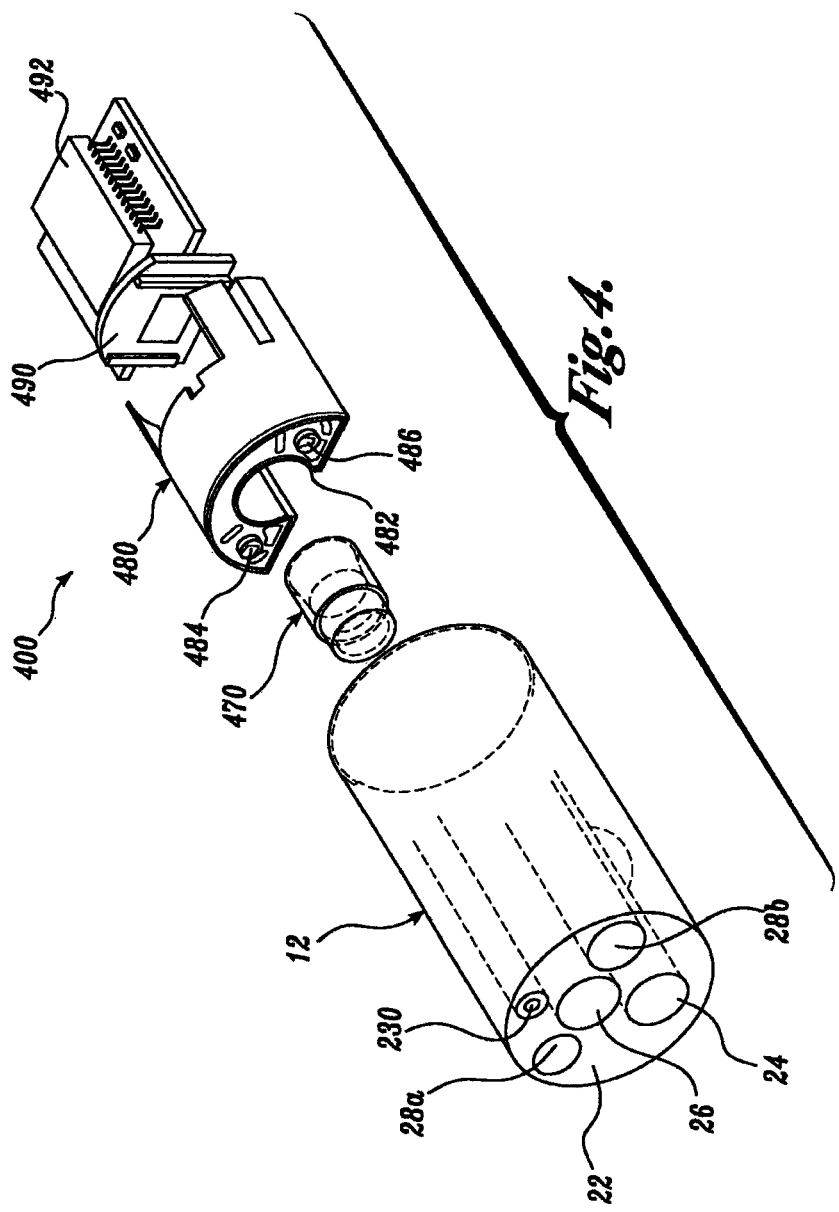

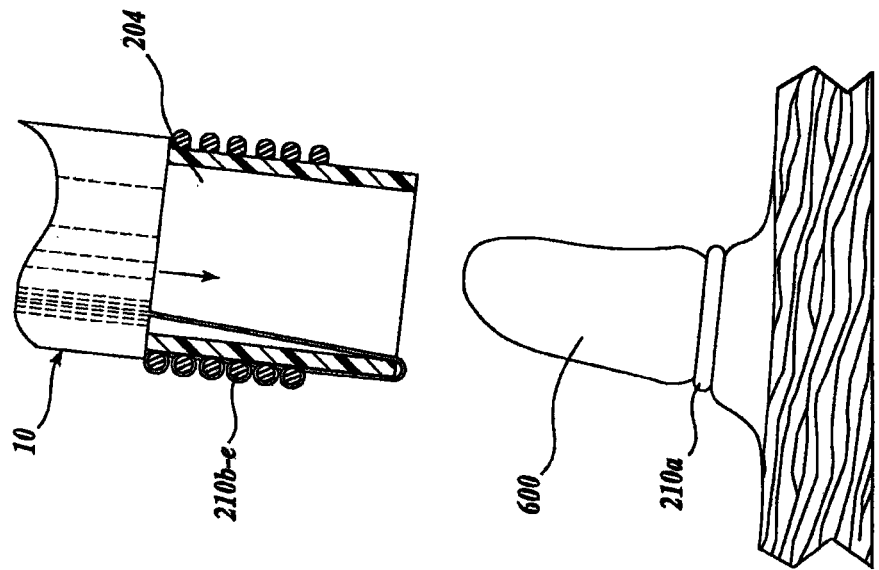
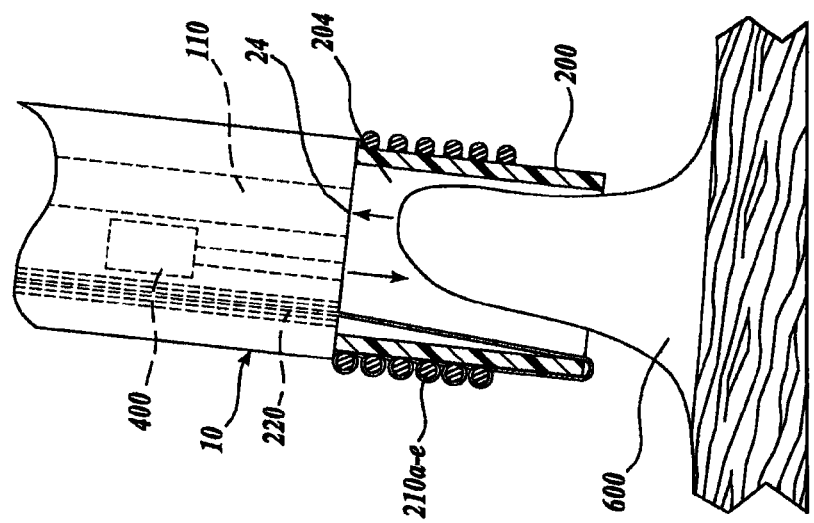

ENDOSCOPIC APPARATUS WITH INTEGRATED VARICEAL LIGATION DEVICE

This application is a continuation of application Ser. No. 11/129,225, filed May 13, 2005, now U.S. Pat. No. 8,097,003 which is relied upon and incorporated herein by reference.

FIELD OF THE INVENTION

The present invention generally relates to medical devices and in particular to variceal banding devices.

BACKGROUND OF THE INVENTION

It has become well established that there are major public health benefits from regular endoscopic examinations as an aid to the early detection of disease of internal structures such as the alimentary and excretory canals and airways, e.g., the colon, esophagus, lungs, uterus, bladder, bronchi, and other organ systems. A conventional imaging endoscope used for such procedures comprises a flexible elongated tube with a fiber optic light guide that directs illuminating light from an external light source to the distal tip where it illuminates the region (i.e., tissue, varices) to be examined. Frequently, additional optical components are incorporated to adjust the spread of the light exiting the fiber bundle and the distal tip. An objective lens and fiber optic imaging light guide communicating with a camera at the proximal end of the scope, or an imaging camera chip at the distal tip, produce an image that is displayed to the operator. In addition, most endoscopes include one or more working channels through which medical devices such as biopsy forceps, snares, fulgration probes, and other tools may be passed.

Conventional endoscopes are expensive hand assembled medical devices costing in the range of $25,000 for an endoscope and much more for the associated operator console. Because of this expense, these conventional endoscopes are built to withstand repeated disinfections and use upon many patients. Conventional endoscopes are generally built of sturdy materials, which decreases the flexibility of the scope and thus can decrease patient comfort. Furthermore, conventional endoscopes are complex and fragile instruments that frequently need expensive repair as a result of damage during use or during a disinfection procedure.

Low cost, disposable medical devices designated for a single use have become popular for instruments that are difficult to sterilize or clean properly. Single-use, disposable devices are packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction and sterilization. One medical device that has not previously been inexpensive enough to be considered truly disposable is the endoscope, such as a colonoscope, bronchoscope, gastroscope, duodenoscope, etc. Such a single-use or disposable endoscope has now been developed and is described in U.S. patent application Ser. No. 10/811,781, filed Mar. 29, 2004, now patented as U.S. Pat. No. 7,413,543, and in a U.S. Continuation-in-Part patent application Ser. No. 10/956,007, filed Sep. 30, 2004, now patented as U.S. Pat. No. 7,578,786, that are assigned to Scimed Life Systems, Inc., now Boston Scientific Scimed, Inc., and are hereby incorporated by reference.

Vascular and lymphatic malformations, otherwise known as varices, pose an extremely challenging treatment dilemma for physicians and for their patients. If varices burst, they can be obliterated by injecting a drug that turns the varices into sclerotic tissue, known as sclerotherapy. The use of sclerotherapy to treat and prevent active hemorrhage has been demonstrated to be one effective intervention; however, there are potential complications associated with the use of various sclerosing agents, such as post-injection fever, swelling, and varying degrees of discomfort. In view of the potential complications associated with sclerotherapy, the development of endoscopic band ligation is now considered a primary intervention for managing active bleeding. The principle behind the development of endoscopic variceal banding is similar to band ligation of hemorrhoids and involves placing elastic bands around the varices. The object of such ligation is to position an elastic band over the targeted region, stretch a band over the region, and release it so that it contracts, thereby applying inward pressure on the section of tissue caught within the band. The effect of the pressure applied by the band is to stop circulation through the targeted tissue, thereby causing the tissue to die. The body eventually sloughs off the banded tissue, or the tissue may be removed later by an endoscope.

Conventional variceal banding systems typically consist of an outer housing cylinder that is snapped-on, frictionally coupled, or otherwise removably attached to the distal end of a conventional endoscope. An inner banding cylinder is then mounted within the outer housing cylinder, with a single band and an associated trip wire threaded through the biopsy channel of the endoscope. While the method of variceal banding has become increasingly popular among physicians, the conventional banding system has several drawbacks. For example, because the banding systems generally contain a single ligation band, the procedure often involves withdrawing and reloading the device with one or more additional ligation bands. In addition, the conventional systems require the user to manually control the trip wire, thereby resulting in a lack of consistent band deployment. Further, the conventional banding systems have poor visualization capabilities due in part to the limitations of conventional video imaging systems and to the visual obstruction from the banding cylinder. Finally, the conventional banding system is removably attached to a conventional endoscope and, therefore, assembly of the endoscope with the banding device must be done prior to each clinical use followed by disassembly and sterilization of the components after each use.

SUMMARY OF THE INVENTION

To address these and other concerns, in one embodiment the present invention is an imaging endoscope comprising a shaft having a proximal end, a distal end, and a variceal banding apparatus fixedly attached to the distal end. The variceal banding apparatus includes a substantially cylindrical hood adapted to receive a plurality of ligation bands. A trigger cable capable of individually deploying each ligation band extends from proximal end of the shaft to the hood. In some embodiments, the endoscope is a single-use endoscope. In another embodiment, the present invention is a system that includes an imaging endoscope having an integrated variceal banding apparatus, a control unit having an actuator capable of tensioning a trigger cable connected to the variceal banding apparatus, and a user input device. In operation of the system, the control unit receives commands from the user input device and digitally actuates the actuator, thereby deploying a ligation band. In another embodiment, the endoscope includes a manual handle with a trigger for actuating the trigger cable, thereby deploying a ligation band. In some embodiments, the system further comprises means for tracking the number of ligation bands remaining on the variceal banding apparatus.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 3C is a side view of another embodiment of a variceal banding apparatus showing an alternative arrangement of the trigger cable and ligation bands;

FIG. 3D is a cross-sectional view of the variceal banding apparatus shown in FIG. 3C;

FIG. 4 illustrates an embodiment of an imaging assembly for use with the variceal banding endoscope in accordance with an embodiment of the present invention;

FIG. 7A illustrates a method of using the variceal banding endoscope to ligate a varix in accordance with an embodiment of the present invention; and FIG. 7B illustrates a ligated varix resulting from the method of using the variceal banding endoscope in accordance with an embodiment of the present invention.

DETAILED DESCRIPTION OF THE PREFERRED EMBODIMENT

As used herein, the term "varix" (plural "varices") refers to an abnormally dilated or swollen vein, artery, or lymph vessel, including esophageal varices and paraesophageal varices. Also included are polyps and hemorrhoids, such as anorectal hemorrhoids or any other tissue that requires removal.

As used herein, the term "ligation" refers to the use of an elastic ring to encircle a varix such that pressure is applied to the varix, thereby cutting off blood flow into the varix.

To address the problems associated with conventional variceal banding systems and others, the present invention is an imaging endoscope having an elongated shaft with a proximal and distal end with a variceal banding apparatus fixedly attached at the distal end. The present system provides many advantages over conventional variceal banding systems, some of which will be discussed in more detail below. For example, several advantages of the present system include, but are not limited to, ease of use, superior visualization, increased control over ligation band deployment, improved band retention, and an accurate count on the number of bands deployed in a procedure.

The various embodiments of the endoscope described herein may be used with both re-useable and low cost, disposable endoscopes, such as an endoscope that is sufficiently inexpensive to manufacture such that it can be a single-use device as described in U.S. patent application Ser. Nos. 10/811,781, filed Mar. 29, 2004, and 10/956,007, filed Sep. 30, 2004, now patented as U.S. Pat. Nos. 7,413,543 and 7,578,786, respectively, that are assigned to Scimed Life Systems, Inc., and hereby incorporated by reference.

While the invention is described in terms of a variceal banding system and apparatus, it will be understood by one of skill in the art that the endoscope having the integrated variceal banding apparatus is a multifunctional device that may also be used for a variety of different diagnostic and interventional procedures, including colonoscopy, upper endoscopy, bronchoscopy, thoracoscopy, laparoscopy, and video endoscopy, etc., in addition to variceal ligation. Additionally, the variceal banding system may use such banding techniques on other tissue, and thus, is not limited to treatment of varices.

Figure 1A:
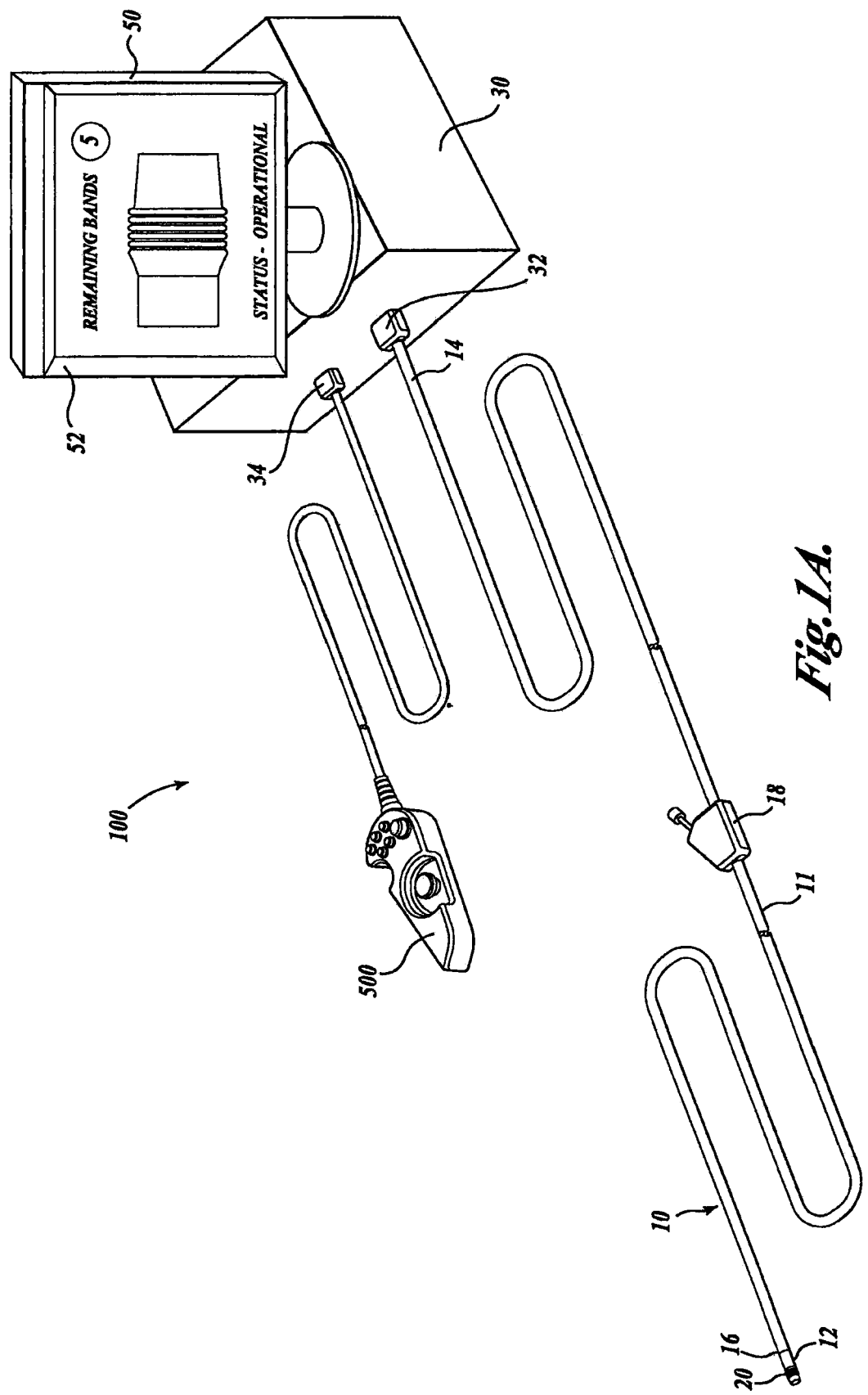
FIG. 1A is a schematic diagram of an endoscope system comprising a variceal banding endoscope connected to a control unit having a user input device and a display in accordance with an embodiment of the present invention.

FIG. 1A illustrates the major components of an exemplary endoscope variceal banding system 100 according to an embodiment of the present invention. The components of the system 100 include a variceal banding endoscope 10 comprising an elongated shaft 11 having a distal end 12 and a proximal end 14. The distal end 12 includes an imaging system, and the proximal end 14 is removably attachable to a connector 32 on a control unit 30. Proximal to the distal end 12 is an articulation joint 16 that provides sufficient flexibility to the articulation section of the shaft 11 such that the distal end 12 can be directed over a required deflection range (e.g., 180° or more) by a steering mechanism and can be directed to make that bend in any direction desired about the circumference of the distal end 12. As shown in FIG. 1A, attached to the distal end 12 is a variceal banding apparatus 20, as will be described in more detail below. The endoscope 10 further includes a set of control cables (not shown) that control the motion of the distal end 12. The ends of the control cables are attached at or adjacent the distal end and run the length of the endoscope 10 while the proximal ends are connected to actuators (not shown) in the control unit 30.

In the embodiment of the system 100 shown in FIG. 1A, the endoscope 10 also includes a breakout box 18 that is positioned approximately midway along the length of the shaft 11. The breakout box 18 provides an entrance to a working channel and may include an attachment point for a vacuum collection bottle (not shown) that collects liquids, debris, or specimens received from the working channel within the endoscope. The working channel is also a conduit for receiving tools to take biopsies, applying therapeutic agents, or performing other medical procedures. Thus, medical devices such as biopsy forceps, snares, fulguration probes, and other tools may be passed through the breakout box 18 and into the endoscope 10.

The endoscope system 100 also includes a user input device 500 having a number of switches that is in communication via a wireless or wired connection to the control unit 30 via a user input device interface 34. In operation of the system 100, a user triggers one or more switches on the user input device 500 to deploy ligation bands from the variceal banding apparatus 20, as well as other commands such as position commands, vacuum, irrigation and the like. The control commands from the user input device 500 are supplied to a processor (not shown) in the control unit 30. The processor in turn sends commands to one or more actuators, such as servo controllers (not shown) in the control unit 30 that control the endoscope steering system and variceal banding apparatus 20, as will be described in further detail below. The control unit 30 also includes a display 50 for displaying a graphical user interface 52 that shows the status of the number of bands remaining on the banding apparatus, as well as images from the imaging system at the distal end 12 and other information related to the endoscope system 100.

Figure 1B:
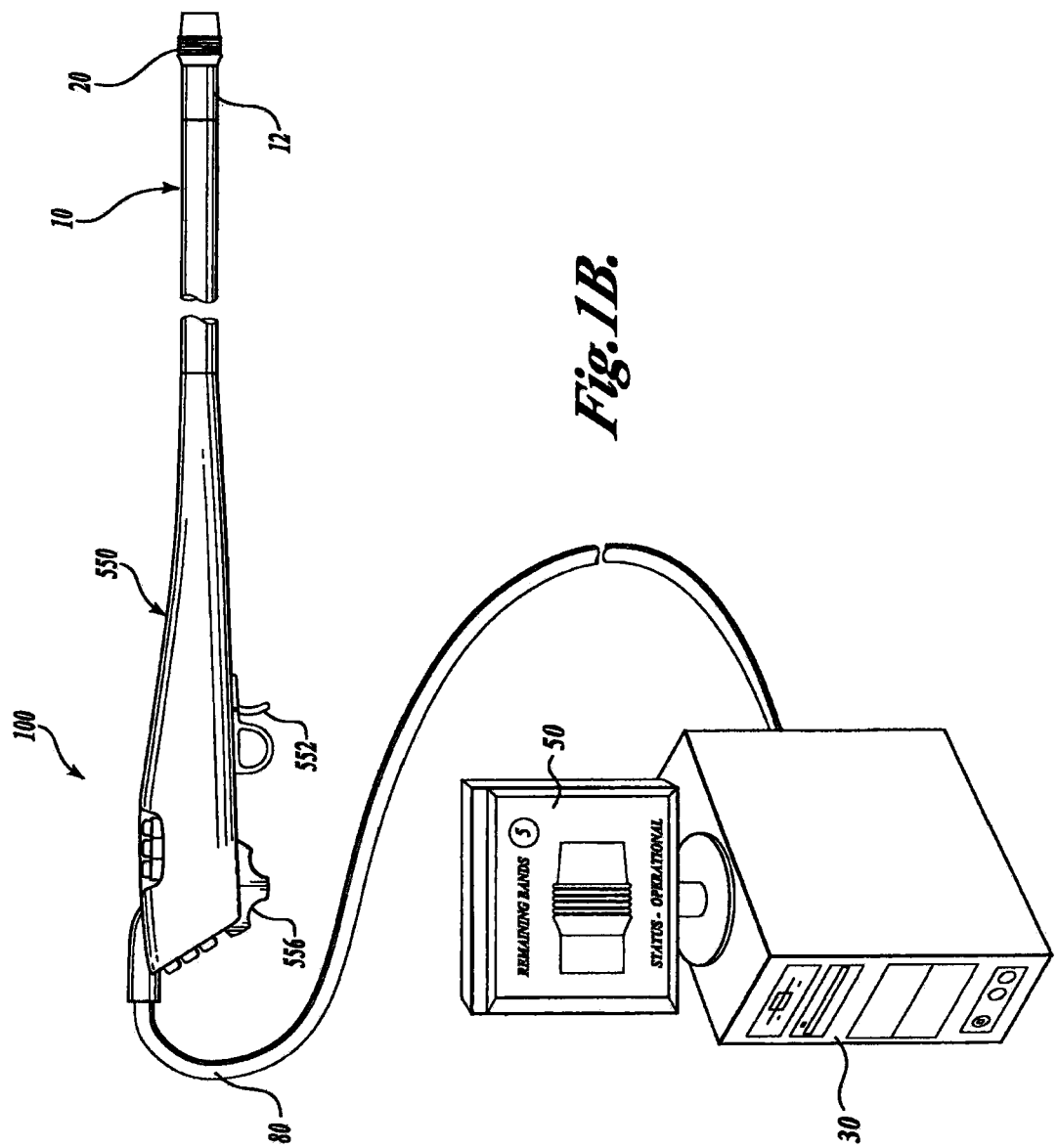
FIG. 1B is a schematic diagram illustrating an endoscope system comprising a variceal banding endoscope that includes a manual handle in accordance with an embodiment of the present invention.
Figure 1C:
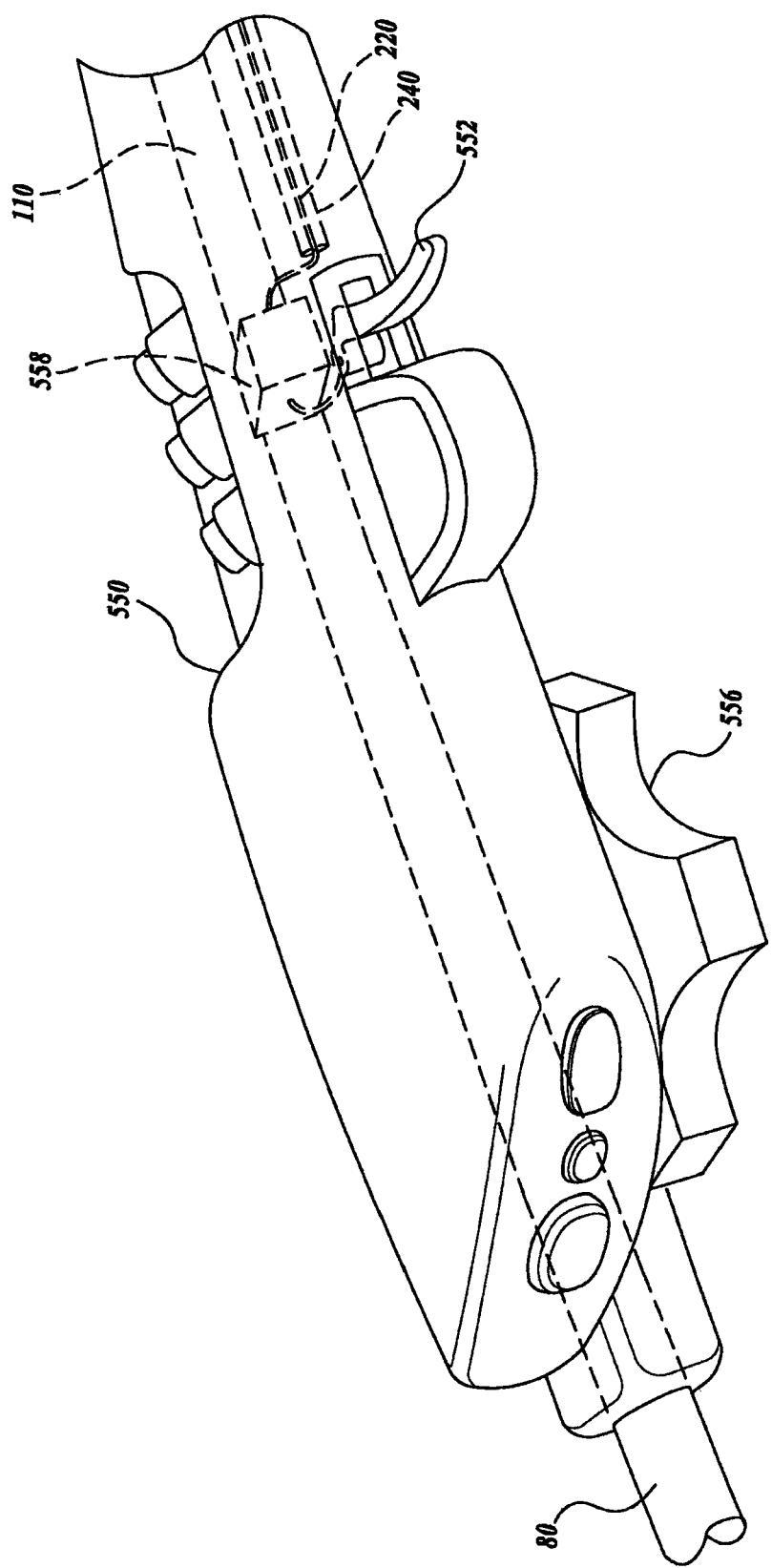
FIG. 1C is a schematic diagram of the manual handle on the endoscope, the handle having a trigger for actuating the trigger cable to deploy a ligation band from the variceal banding endoscope in accordance with an embodiment of the invention.

FIG. 1B illustrates another embodiment of the endoscope variceal banding system 100 comprising a variceal bander endoscope 10 that includes a manual handle 550. The ligation band deployment and other functions of the endoscope (e.g., steering, vacuum, irrigation and the like) may be controlled by the handle 550, which is, in turn, connected to the control unit 30 via a conduit 80. As best shown in FIG. 1C, the handle 550 contains a manually actuated steering mechanism 556 for effecting 4-way steering of the distal end 12 in the up/down (via an inner knob) and right/left directions (via an outer knob). The knobs 556 are connected to the proximal ends of control cables (not shown) that extend through the endoscope shaft so that rotation of the knobs selectively tightens or relaxes the control cables in order to bend the distal end 12. As shown in FIG. 1C, a trigger 552 is located in the handle 550 that provides an input signal to an actuator 558 that actuates the trigger cable 220 with a predetermined, reproducible force. The trigger 552 provides user control over the variceal banding apparatus 20 located at the distal end of the endoscope via the actuator 558 and the trigger cable 220. The actuator 558 may be any type of actuator capable of actuating the trigger cable 220 with a predetermined, reproducible force, such as, for example, a pneumatic, hydraulic, electro-motive, solenoid actuator, or other driver mechanism. In an alternative embodiment, the trigger 552 may be configured to deliver a predetermined, reproducible force by a spring-loaded, pre-set stop device or ratchet mechanism. While the user input control for ligation band deployment has been described in terms of a trigger mechanism, it will be understood by one of skill in the art that other types of controls on the handle 550 as possible, such as rotating controls, push buttons, hydraulic, pneumatic controls and the like.

With continued reference to FIG. 1C, the handle 550 is coupled to the control unit 30 with a flexible shaft through which a conduit 554 passes. The conduit 554 carries image information back to the imaging electronics housed in the control unit 30 from the imaging sensor in the distal end 12 of the endoscope 10. In one embodiment, the manual handle 550 includes additional control switches and manifold(s) for operating various control functions of the endoscope 10 as described in U.S. patent application Ser. No. 10/955,910, filed Sep. 30, 2004, assigned to Scimed Life Systems, Inc. and hereby incorporated by reference.

Figure 2:
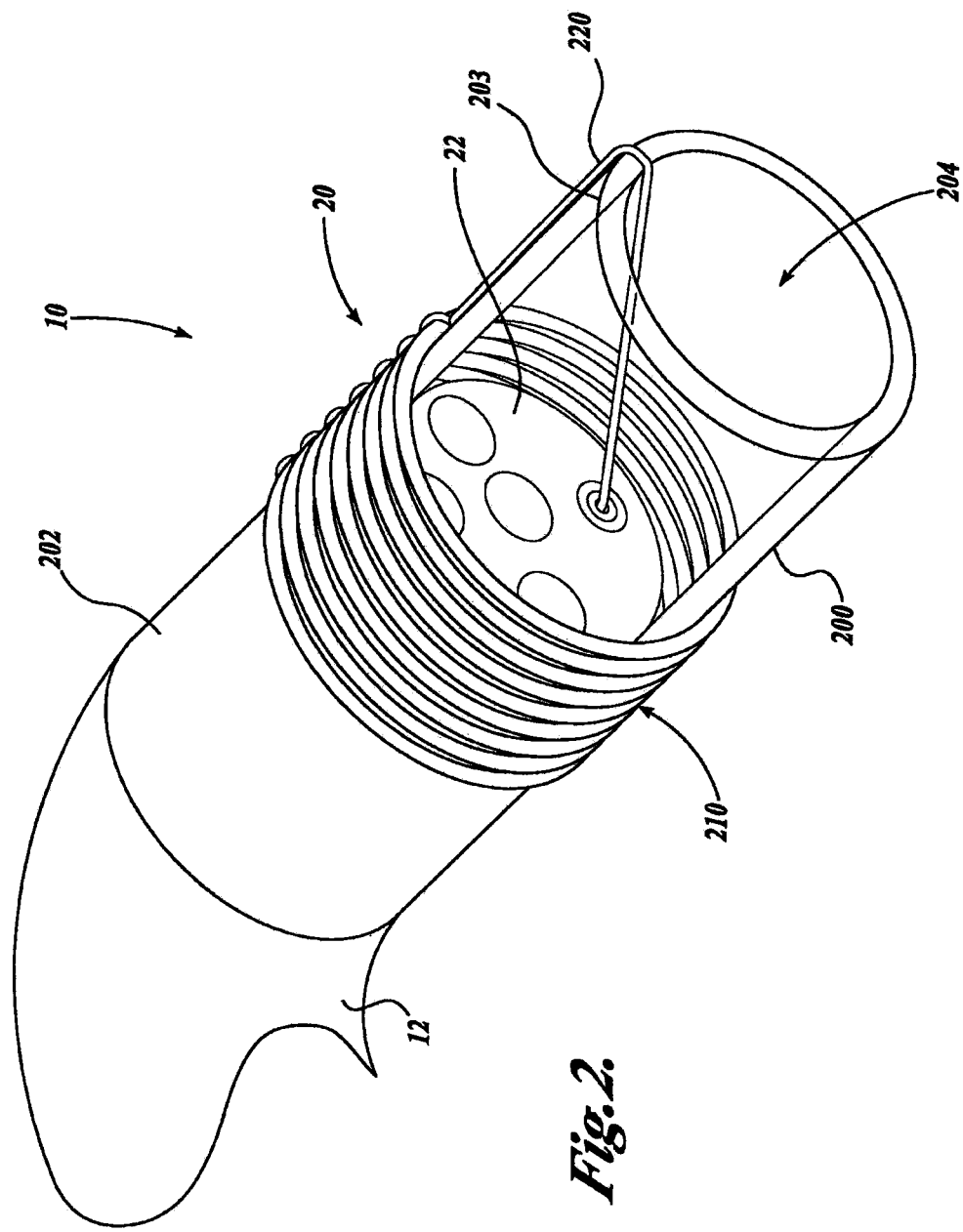
FIG. 2 is a perspective view showing a representative embodiment of a variceal banding apparatus attached to the distal end of a variceal banding endoscope in accordance with an embodiment of the present invention.

FIG. 2 is a partial perspective view of the endoscope 10 showing more detail of the variceal banding apparatus 20 attached to the distal end 12 of the endoscope 10. Fitted into the distal end 12 of the shaft 11 is a distal face 22 having a number of ports including an imaging port that houses an imaging system, as will be described in more detail below. Attached to the distal end 12 is the variceal banding apparatus 20 that includes a hood 200 having a proximal end 202 that is fixedly attached to the distal end 12 of the shaft 11. The attachment between the hood 200 and the shaft 11 may be by any suitable means. In some embodiments, the hood 200 is integrally formed with the walls of the shaft 11. In other embodiments, an adhesive, fasteners, or the like is used to provide a permanent attachment. As shown in FIG. 2, the distal end 203 of the hood 200 protrudes beyond the distal face 22, thereby creating an open cavity 204. In operation, the cavity 204 provides an area into which a varix to be ligated may be drawn, for example, by vacuum or an instrument, so that a ligation band released from the outer surface of the hood 200 will encircle and grip the varix such that the band will remain on the varix and ligate it after the varix has been released.

With continued reference to FIG. 2, a plurality of ligation bands 210 are disposed around the outer surface of the hood 200. In the exemplary embodiment shown in FIG. 2, the ligation bands 210 are disposed towards the proximal end of the hood 203 in order to allow an unobstructed view through the imaging system. The trigger cable 220 is associated with the plurality of ligation bands 210 disposed on the hood 200, extends through the cavity 204 into a lumen 240 (shown best in FIG. 3), and is connected at the proximal end 14 of the endoscope shaft 11 to one or more actuators 558 in the handle 550 and/or in the control unit 30.

In the system 100, the operation of the trigger cable 220 is accomplished digitally by an actuator in the control unit 30 which is controlled via operator commands entered through the user input device 500. Alternatively, the operation of the trigger cable 220 is accomplished by actuating the trigger 552 on the handle 550, which in turn actuates the trigger cable 220 to deploy a ligation band.

In one embodiment, the hood 200 is preferably made of a transparent, rigid material such that it does not deform, to allow optimal imaging from the imaging system. Suitable materials include, for example, polycarbonate and the like. The hood 200 may have a substantially cylindrical shape or may be formed into any other shape that is adapted to conform to the surface of a tissue containing a varix, such as, for example, a tapered shape. The endoscope shaft 11 and the hood 200 may be formed into a variety of diameters suitable for use in a particular clinical application. In some embodiments, the outer diameter of the hood 200 is in the range of from about 6.0 mm to about 13.0 mm.

The ligation bands 210 may be made of any suitable bio-compatible elastic material that will form a band capable of easily stretching over the largest tissue to be ligated and also securely grip the tissue to be removed. The elastic material preferably has the properties of stretching over a wide diameter while retaining elasticity for a long period of time, such as, for example, rubber materials and elastomeric materials. The number of ligation bands 210 disposed on the outer surface of the hood 200 is chosen based on several factors including the therapeutic application, the outer diameter and dimensions of the hood 200, and the thickness of the ligation bands. In one exemplary embodiment, the hood 200 is adapted to receive at least eight ligation bands. In another embodiment, the hood 200 is adapted to receive at least five ligation bands. In yet another embodiment, the hood 200 is adapted to receive at least two ligation bands. Other numbers of bands are also contemplated to be within the scope of the present invention. In some embodiments, the ligation bands 210 may also include a coating or composition containing a therapeutic agent such as a hemostatic agent or an anti-inflammatory agent.

In some embodiments, the system 100 includes means for mapping position coordinates of the varix that has been ligated. In some embodiments, means for mapping the ligated varix includes identification indicia on the ligation bands 210, such as, for example, one or more predetermined colors, one or more codes, an embedded tag such as an RFID tag, or other means for determining location and/or order of deployment within a patient. The position coordinates of the ligated varices may also be obtained using imaging methods such as x-ray or ultrasound technologies that are well known to those of skill in the art. In some embodiments, the endoscope 10 further comprises a position sensor receiver element (not shown) that is tracked by a tracking system using electromagnetic radiation transmitted by two or more external antenna. For example, an electromagnetic sensor element and antenna as described in U.S. Pat. No. 6,593,884 may be used, which is hereby incorporated by reference.

Figure 3A:
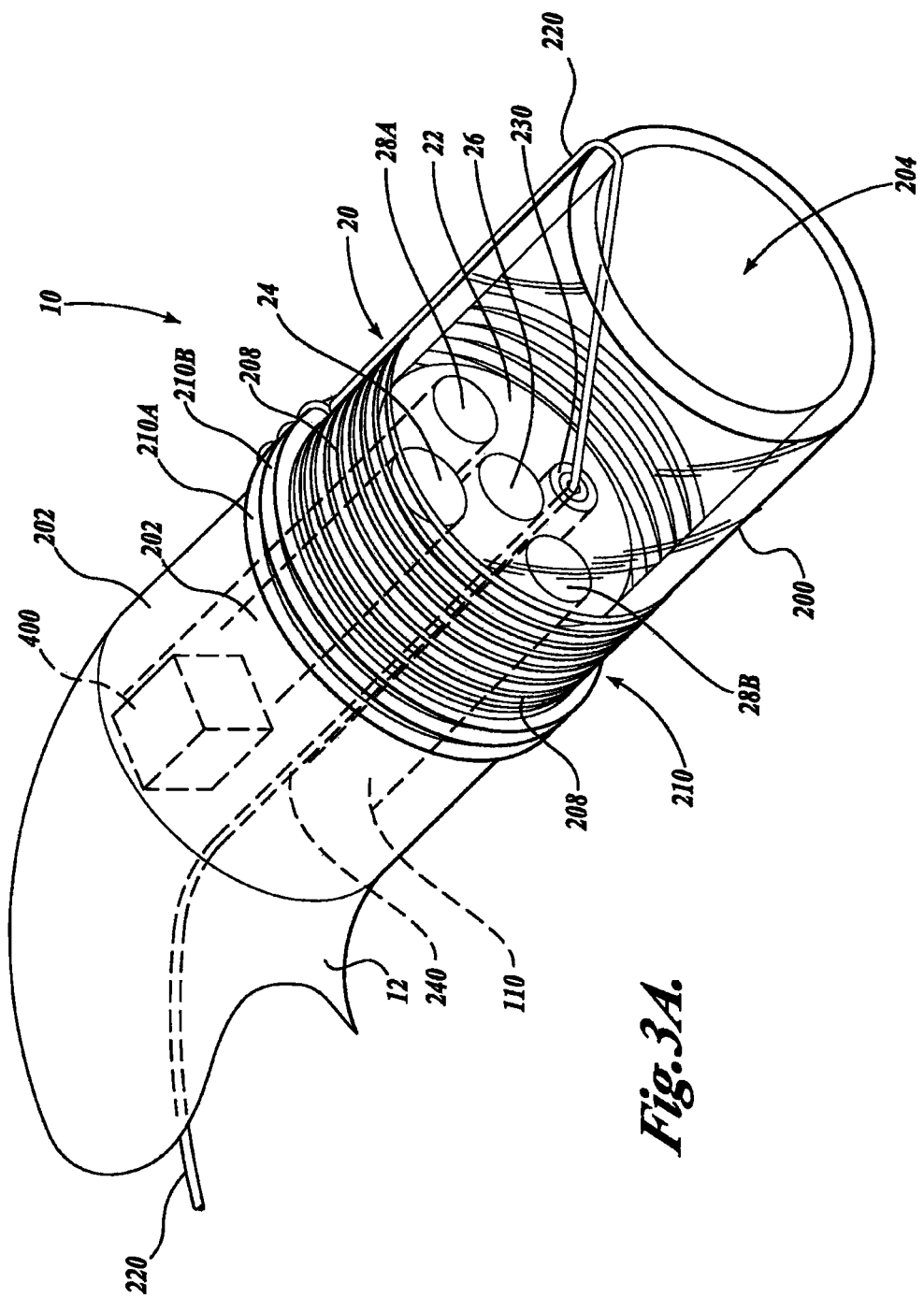
FIG. 3A is a partial cut-away view of a representative embodiment of a variceal banding apparatus attached to the distal end of the variceal banding endoscope showing a transparent hood loaded with several ligation bands and a trigger cable extending into the proximal end of the endoscope having a working channel and an imaging system in accordance with an embodiment of the present invention.
Figure 3B:
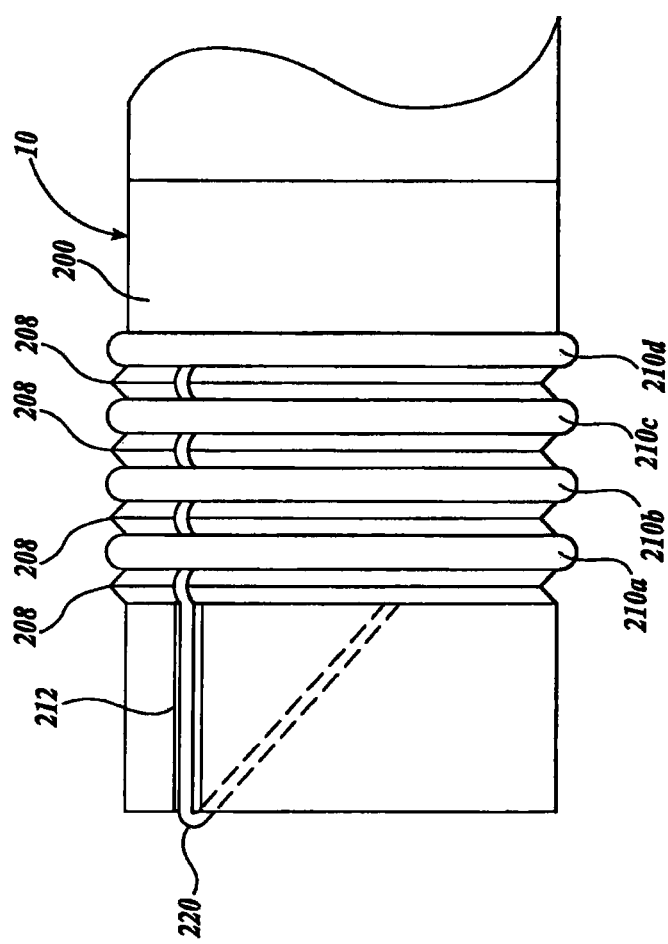
FIG. 3B is a front view of a representative embodiment of a variceal banding apparatus showing a more detailed view of an arrangement of the trigger cable and several ligation bands in accordance with an embodiment of the invention.

FIG. 3A is a partial cutaway view of an embodiment of the variceal banding apparatus 20 attached to the distal end 12 of the variceal banding endoscope 10. In the embodiment shown in FIG. 3A, the variceal banding apparatus 20 includes the hood 200 containing two ligation bands 210A and 210B. As best shown in FIG. 3B, the hood 200 further includes an optional ligation band retaining structure 208 that secures the bands 210A, 210B, 210C and 210D thereto. In some embodiments, the hood further includes an optional groove 212 formed in the exterior of the hood 200 to secure the trigger cable 220.

The trigger cable 220 is associated with each ligation band 210 such that each ligation band 210 is individually released upon the actuation of the trigger cable 220 with a predetermined force. For example, in one embodiment, as shown in FIG. 2, the trigger cable 220 is physically arranged around each ligation band 210 in succession in such a way that each ligation band 210 is released from hood 200 and also released from the trigger cable 220 upon actuation of the trigger cable 220. In another embodiment, a single trigger cable 220 may be divided into a plurality of attachments. In yet another embodiment, a separate trigger cable 220 may be provided for each of the bands 210.

As shown in FIG. 3A and FIG. 3B, in one exemplary embodiment, the trigger cable 220 extends from the lumen 240 in the groove 212 and is arranged around each retaining structure 208 and under each ligation band 210A, 210B, 210C and 210D, such that ligation band 210A is the first ligation band that will be deployed upon tension of the trigger cable 220.

In an alternative embodiment, as shown in FIG. 3C, the retaining structures 208A, 208B, and 208C are raised, compressible structures that are held in place by compressing elements 209A, 209B and 209C. The compressing elements 209A, 209B and 209C are wrapped around each retaining structure 208A, 208B and 208C and each extend through the hood 200 in a looped configuration. As shown best in FIG. 3D, the trigger cable 220 extends through the lumen 240 and is attached to the loop of each compressing element 209A, 209B and 209C from the interior of the hood 200. Each attachment point between the trigger cable 220 and the loop of the compressing elements 209 is selected to allows for a predetermined amount of slack between the trigger cable 220 and each loop on element 209A, 209B and 209C. In operation, the user actuates the trigger 552, thereby actuating the trigger cable 220 which applies a predetermined force to the first compressing element 209A. Upon actuation of the trigger cable 220, the first compressing element 209A is pulled downward towards the surface of the hood 200, thereby compressing the retaining structure 208A, which in turn allows the ligation band 210A to be released off the hood 200 and onto the varix positioned in the cavity 204. It will be understood by one of skill in the art that alternative designs for securing the ligation bands 210 are also possible, such as multiple grooves cut into the outer surface of the hood 200 and the like.

With reference now to FIG. 3A, the distal face 22 includes a number of ports, including an access port 24 that defines the entrance to a working channel lumen 110, an imaging port 26 containing an imaging lens, and illumination ports 28 containing illumination port lenses. Also included on the distal face 22 is an entrance port 230 to a trigger cable lumen 240. In some embodiments, the distal face 22 may include additional ports such as a camera lens flushing port that directs air or a cleaning fluid such as water over a lens in the camera port 26. The working channel port 24 connects to the working channel 110 that extends along the shaft 11 of the endoscope 10. The working channel 110 is used for applying a vacuum and may be also used for passing tools such as forceps, insufflation, or irrigation, including lens washing.

As mentioned above, the distal end 12 of the single-use endoscope 10 includes an imaging assembly 400 housed within the imaging port 26. FIG. 4 shows further detail of one embodiment of the imaging assembly 400 that may be practiced with the present invention. The imaging assembly 400 is located at the distal end 12 of the variceal banding endoscope 10. As shown in FIG. 4, fitted within the imaging port 26 is an imaging lens assembly 470. The imaging lens assembly 470 is fitted within a heat exchanger 480. An image sensor 490 is secured to the proximal end of the heat exchanger 480 to record images focused by the imaging lens assembly 470. The image sensor 490 is preferably a low light sensitive, low noise, CMOS color imager with VGA resolution or higher such as SVGA, SXGA or XGA. The video output is preferably in digital format. In some embodiments, the image sensor 490 comprises a VGA CMOS image sensor with 640×480 active pixels and an on-chip serializer that transmits image data to the control unit 30 in a serial format. Such a CMOS image sensor is available as Model No. MI-370 from Micron Electronics of Boise, Id. Further detail of an exemplary imaging system can be found in U.S. Pat. No. 10/811,781, filed Mar. 29, 2004, and in U.S. Continuation-in-Part patent application Ser. No. 10/956,007, filed Sep. 30, 2004, that are assigned to Scimed Life Systems, Inc., and which are hereby incorporated by reference.

With continued reference to FIG. 4, a pair of light emitting diodes ("LEDs") 484 and 486 are bonded to a circuit board (not shown) that is bonded to a front surface of the heat exchanger 480 such that a channel is formed behind the circuit board for the passage of a fluid or gas to cool the LEDs. The imaging lens assembly 470, the LEDs 484 and 486, and the image sensor 490 and associated circuitry (not shown) secured in the heat exchanger 480 are fitted within the distal end 12 of the endoscope 10. Although the embodiment of the distal end 12, shown in FIG. 4, shows two LEDs 484 and 486 that are positioned on either side of the lens assembly 470, it will be appreciated that additional LEDs could be used and corresponding changes made to the shape of the illumination ports 28A and 28B, positioned in front of the LEDs. As an alternative to LEDs, the light source for the endoscope 10 may be external to the endoscope such that the illumination light is delivered to the illumination port with a fiber optic bundle of a light carrying device. In operation, the imaging assembly 400 in combination with the transparent hood 200 fixedly coupled to the distal end 12 of the shaft 11 provides improved visualization of a varix before, during, and after variceal ligation in comparison to conventional variceal ligation systems.

Returning to FIG. 1A, in one embodiment, the proximal end 14 of the shaft 11 is connected to the control unit 30 with the connector 32. The connector 32 carries image information back to imaging electronics housed in the control unit 30 from the imaging sensor 490. The video data provided to the control unit 30 by the image sensor 490 may be placed in a suitable format for display on the monitor 50 for viewing by the operator. The connector 32 further carriers power for LED illumination forward from the control unit 30 to the endoscope 10, as well as carrying irrigation/insufflation fluids forward through the shaft 11 to the distal end of the endoscope 10. Vacuum pressure is also provided to the working channel 110 through the connector 32.

Figure 5:
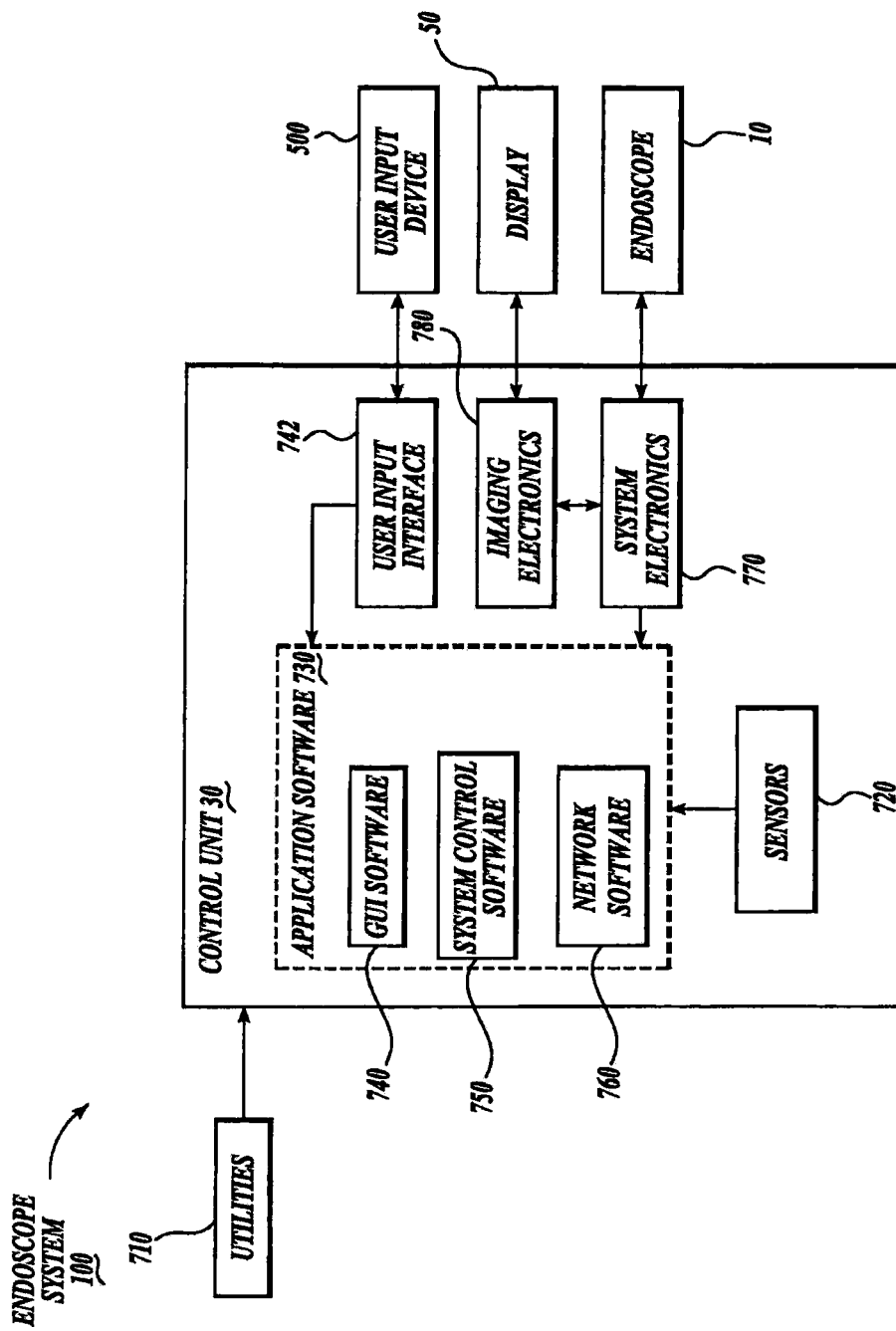
FIG. 5 is a block diagram of one embodiment of a control unit for use with the endoscope system of FIG. 1A formed in accordance with aspects of the present invention.

FIG. 5 is a block diagram of one exemplary embodiment of the control unit 30 for use in the system 100. The control unit 30 is connected to a source of electrical power, as well as to a plurality of utilities 710, including, for example, but not limited to, an irrigation source, an aeration supply, and a source of vacuum. The control unit 30 further includes a processor (not shown), one or more sensors 720, and a suite of application software 730. The application software 730 further includes a graphical user interface (GUI) software application 740, a system control software application 750, and may additionally include a network software application 760. In addition, the control unit 30 may include a manifold (not shown), a series of system electronics 770, and an imaging electronics board 780.

The GUI software application 740 is connected to the user input device 500 via a user input interface 742. The user input device 500 may contain GUI navigational controls to allow a user to determine the status of one or more system 100 operating parameters, such as, for example, the number of bands on the hood 200. In some embodiments of the system 100, the GUI software 740 provides the operator with the status of number of ligation bands 210 remaining on the hood 200 and displays the number of bands remaining on the display 50, as shown in FIG. 1A. In some embodiments, the GUI software application 740 also provides the operator with live endoscopic video images.

The sensors 720 may include, for example, pressure transmitters, and temperature sensors, and are used for real-time electronic feedback of hardware operating parameters, such as pressure and temperature. In one embodiment, the system 100 includes a band sensor device located on the hood 200, such as, for example, a pressure sensor that sends a signal to the control unit 30 corresponding to the presence or absence of a band 210 on the hood 200. In another embodiment, the application software 730 in the control unit 30 includes software provisions that interface with the user input interface 742 and the user input device 500 such that the number of ligation band 210 deployments initiated by the switch on the user input device 500 are recorded, tallied, and displayed on the graphical user interface 52.

Figure 6:
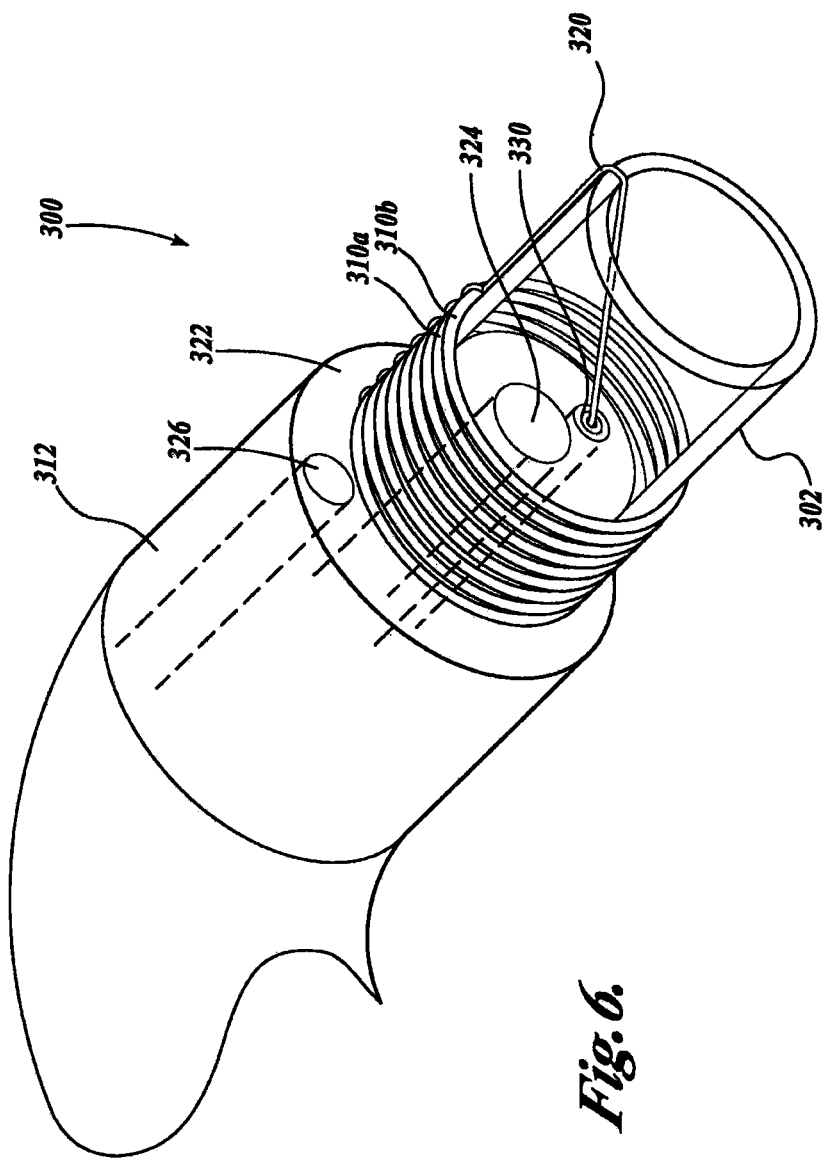
FIG. 6 illustrates another embodiment of a variceal banding apparatus attached to the distal end of a variceal banding endoscope in accordance with the present invention.

FIG. 6 illustrates an alternative embodiment of an endoscope 300 formed in accordance with aspects of the present invention. The endoscope 300 is substantially similar in materials, construction, and operation to endoscope 10, except for the differences that will now be described. As shown in FIG. 6, the distal end 312 of the shaft has a distal face 322. A transparent hood 302 protrudes distally from the distal face 322 and has a smaller diameter than the outer diameter of the shaft 312 such that it encircles a portion of the distal face 322.

In the embodiment shown in FIG. 6, the hood 302 encircles a working channel port 324 and a trigger cable port 330 that houses a trigger cable 320.

As further shown in FIG. 6, a plurality of ligation bands 310A and 310B are disposed around the hood 302. An imaging port 326 is positioned on the distal face 322 such that it is outside of the hood 200. The imaging port 326 may contain one or more imaging lenses and imaging system as previously described, or alternatively, a fiber optic light guide may be passed through the imaging port 326 to allow imaging of a varix through the transparent hood 302. In the embodiment of the endoscope 300 shown in FIG. 6, the reduced diameter of the hood 302 in relation to the outer diameter of shaft 312 allows the use of smaller diameter ligation bands 310 with a larger diameter endoscope 300.

As mentioned above, in some embodiments, the variceal banding endoscope 10 is a single-use endoscope. The single-use endoscope 10 and ligation bands 210 may be packaged as a kit for variceal band ligation. In some embodiments, the single-use variceal endoscope 10 is packaged in a sterile wrapper at the time of manufacture. The ligation bands 210 may be preloaded on the hood 200 prior to packaging or may be packaged in a separate sterile wrapper. In such embodiments, the single-use endoscope 10 may further contain a memory having stored information such as the initial number of bands 210 and/or software provisions that interface with the control unit 30 regarding the method for determining the number of ligation bands contained on the variceal banding apparatus. Stored information, such as a program or data, may be programmed into a memory chip at time of manufacture that is embedded into the endoscope 10 and transferred to a processor in the system 100 upon connection of the proximal end of the endoscope to the control unit 30.

In operation, prior to clinical use, a plurality of ligation bands 210 are positioned on the hood 200 of the variceal banding endoscope 10. The trigger cable 220 is arranged around the bands 210 as described above. The proximal end 14 of the endoscope 10 is connected to the control unit 30. In some embodiments of the system 100 the number of ligation bands 210 on the hood 200 is entered into a user interface, such as the user input device 500, or via a input device on the handle 550 by the operator. In other embodiments, the connection of the endoscope 10 to the control unit 30 triggers an information transfer to the control unit 300, including the number of ligation bands loaded on the hood 200. Once the ligation bands 210 are loaded and the number of bands on the hood 200 is recorded in the system 100, the variceal banding procedure may be initiated.

FIG. 7A illustrates a view of an exemplary single-use endoscope 10 inserted into a patient, with the hood 200 loaded with five ligation bands 210A, 210B, 210C, 210D, 210E inserted into a patient. As described above, live images of the patient's tissue surrounding the distal end of the endoscope are captured by the imaging apparatus 400 during the procedure and are displayed on the display 50. At any point during the procedure, the operator may activate the user interface 52 via the user input device 500 to determine the number of remaining ligation bands 210 on the hood 200. As shown in FIG. 7A, when the operator observes the image of a varix 600 that needs to be ligated, the operator maneuvers the endoscope 10 into position by the steering mechanism so that the hood 200 is adjacent to the varix 600. The operator then applies a vacuum through the working channel 110 or uses other techniques to pull the varix into the cavity 204 in the hood 200 toward the direction of the working channel port 24. The system 100 preferably has a variable vacuum source to allow for ease of manipulation of the varix. Once the varix 600 is in the desired position, the operator activates a trigger on the user input device 500 which sends a digital command via a processor to an actuator in the control unit 30 that tensions the trigger cable 220 with a preprogrammed force. As shown in FIG. 7B, once the trigger cable 220 is tensioned, the distal-most ligation band 210A is pulled over the hood 200, thereby encircling and ligating the varix 600. Once ligation is achieved, the vacuum is turned off, thereby releasing the ligated varix 600. The treatment of the varix 600 may further include therapeutic manipulation of the tissue with a tool inserted through the working channel 110, such as an injection of a therapeutic agent, such as a hemostatic agent.

In accordance with one embodiment of the system 100, the activation of the trigger on the user input device 500 (or the trigger 552 on the handle 550) is recognized by the control unit 30 and the user interface 52 is automatically reset to show that four ligation bands 210B, 210C, 210D, 210E now remain on the hood 200. Alternatively, in another embodiment, the presence of each ligation band may be determined by a pressure sensor on the hood 200. The procedure may be repeated until all of the ligation bands 210 have been deployed.

Once the procedure has been completed, the proximal end of the endoscope 10 is removed from the control unit 30 and the single-use endoscope 10 is discarded. In accordance with the use of the variceal ligation system 100 of the invention, the ligated varix 600 shrinks over time and eventually sloughs off, leaving a scar in the place of the varix. As described above, in some embodiments the system 100 tracks the coordinates of each ligated varix, allowing an operator to later view the treated regions to verify that healing has occurred.

While the preferred embodiments of the invention have been illustrated and described, it will be appreciated that various changes can be made therein without departing from the scope of the invention.

The embodiments of the invention in which an exclusive property or privilege is claimed are defined as follows:

1. A medical device, comprising:
an elongate shaft having a proximal end and a distal portion;
a plurality of compressible structures disposed on the distal portion and arranged so that each pair of compressible structures defines a space therebetween;
a plurality of compressive elements, wherein each compressive element corresponds to one of the plurality of compressible structures on the distal portion;
a plurality of elastic members, each elastic member disposed in the space between a corresponding pair of adjacent compressible structures; and
an elongate member, wherein a portion of the elongate member is coupled to each compressible structure such that, upon tension of the elongate member, one of the plurality of elastic members is released from the distal portion;
wherein, prior to applying tension to the elongate member, the plurality of compressible structures extend radially outward from an exterior surface of the distal portion; and
wherein, upon tension of the elongate member, one of the plurality of compressible structures is pulled toward the exterior surface of the distal portion.

2. The device of claim 1, wherein the portion of the elongate member coupled to each of the plurality of compressible structures extends through the distal portion in a loop configuration.

3. The device of claim 1, wherein the plurality of elastic members are ligation bands.

4. The device of claim 1, wherein the distal portion is translucent.

5. The medical device of claim 1, wherein each portion of the elongate member that is coupled to each compressible structure is selected to allow for a predetermined amount of slack between the elongate member and each compressible structure.

6. The medical device of claim 1, wherein each compressive element has a loop configuration that encircles a corresponding one of the plurality of compressible structures.

7. The medial device of claim 1, wherein a hood is coupled to the distal portion of the elongate shaft; and
each compressive element has a portion within an interior of the hood.

8. The medical device of claim 1, wherein, prior to applying tension to the elongate member, the portion of the elongate member has a slack confiauration.

9. A medical device, comprising:
a shaft having a proximal end and a distal end;
a hood coupled to the distal end of the shaft, the hood having a plurality of elastic members disposed on the hood and a plurality of compressible structures disposed on the hood, wherein each elastic member is disposed between adjacent compressible structures;
a plurality of compressive elements, wherein each compressive element corresponds to one of the plurality of compressible structures on the hood; and
an elongate member coupled to the plurality of compressive elements such that, upon tension of the elongate member, one of the plurality of elastic members is released from the hood;
wherein, prior to applying tension to the elongate member, the plurality of compressible structures extend radially outward of an exterior surface of the hood; and
wherein, upon tension of the elongate member, one of the plurality of compressible structures is compressed toward the exterior surface of the hood.

10. The device of claim 9, wherein each compressive element is arranged around the corresponding one of the plurality of compressible structures.

11. The device of claim 9, wherein each compressive element has a loop configuration.

12. The device of claim 9, wherein each compressive element has a portion within an interior of the hood.

13. The device of claim 12, wherein, prior to applying tension to the elongate member, the portion has a slack configuration.

14. A medical system, comprising:
a medical device having a proximal end and a distal end;
a plurality of compressible structures disposed on the distal end and arranged so that each pair of compressible structures defines a space therebetween, wherein each compressible structure includes a compressive element configured to press against a corresponding compressible structure extending radially outward from an exterior surface of the distal end;
a plurality of elastic members, each elastic member disposed in the space between a corresponding pair of adjacent compressible structures; and
an elongate member coupled to each compressive element; and
a control unit including an actuator configured to apply tension to the elongate member, thereby causing each of the compressive element to pull a corresponding compressible structure toward the exterior surface of the medical device.

15. The system of claim 14, wherein, upon tension of the elongate member, an elastic member closest to a distalmost end of the medical device is released from the medical device.

16. The system of claim 14, wherein, upon tension of the elongate member with a predetermined force, each elastic member is released individually from the medical device.

17. The system of claim 14, wherein the system further includes a processor configured to track position coordinates of a varix that has been ligated.

18. The system of claim 14, wherein the medical device includes an imaging system adjacent the distal end of the medical device.

19. The system of claim 14, further including a sensor located adjacent the distal end of the medical device, wherein the sensor is configured to sense the position of each of the plurality of elastic members on the distal end of the medical device.

* * * * *

UNITED STATES PATENT AND TRADEMARK OFFICE
CERTIFICATE OF CORRECTION

PATENT NO. : 8,585,715 B2  
APPLICATION NO. : 13/325638  
DATED : November 19, 2013  
INVENTOR(S) : David W. Hoffman et al.

It is certified that error appears in the above-identified patent and that said Letters Patent is hereby corrected as shown below:

In the Claims:

Claim 7, col. 12, line 11, currently reads "medial" but instead should read "medical".

Signed and Sealed this
Eighteenth Day of March, 2014

Michelle K. Lee
*Deputy Director of the United States Patent and Trademark Office*